(12) United States Patent
Burczynski et al.

(10) Patent No.: US 7,643,943 B2
(45) Date of Patent: Jan. 5, 2010

(54) METHODS FOR MONITORING DRUG ACTIVITIES IN VIVO

(75) Inventors: Michael E. Burczynski, Collegeville, PA (US); Joseph Boni, Wayne, PA (US); Andrew J. Dorner, Lexington, MA (US); Natalie C. Twine, Goofstown, NH (US); Jennifer Stover, Topsfield, MA (US); William L. Trepicchio, Andover, MA (US); Virginia Fitzpatrick, Norristown, PA (US); Fred Immermann, Suffern, NY (US)

(73) Assignee: Wyeth LLC, Madison, NJ (US)

( * ) Notice: Subject to any disclaimer, the term of this patent is extended or adjusted under 35 U.S.C. 154(b) by 319 days.

(21) Appl. No.: 10/793,032

(22) Filed: Mar. 5, 2004

(65) Prior Publication Data

US 2004/0235020 A1 Nov. 25, 2004

Related U.S. Application Data

(63) Continuation-in-part of application No. 10/775,169, filed on Feb. 11, 2004.

(60) Provisional application No. 60/446,133, filed on Feb. 11, 2003, provisional application No. 60/459,782, filed on Apr. 3, 2003, provisional application No. 60/538,246, filed on Jan. 23, 2004.

(51) Int. Cl.
*G01N 33/48* (2006.01)
(52) U.S. Cl. ...................................................... 702/19
(58) Field of Classification Search .................... 702/19
See application file for complete search history.

(56) References Cited

U.S. PATENT DOCUMENTS

| | | | |
|---|---|---|---|
| 5,840,506 A | 11/1998 | Giordano | |
| 6,087,098 A | 7/2000 | McKiernan et al. | |
| 6,110,675 A | 8/2000 | Cohen et al. | |
| 6,190,857 B1 | 2/2001 | Ralph et al. | |
| 6,288,220 B1 | 9/2001 | Kambara et al. | |
| 6,303,301 B1 | 10/2001 | Mack et al. | |
| 6,317,731 B1 | 11/2001 | Luciano | |
| 6,391,562 B2 | 5/2002 | Kambara et al. | |
| 6,647,341 B1 | 11/2003 | Golub et al. | |
| 2001/0053548 A1 | 12/2001 | Rybak et al. | |
| 2002/0042072 A1 | 4/2002 | Van Meel et al. | |
| 2002/0132274 A1 | 9/2002 | Nevalainen et al. | |
| 2002/0164664 A1 | 11/2002 | Hlavaty et al. | |
| 2002/0168638 A1 | 11/2002 | Schlegel et al. | |
| 2002/0182614 A1 | 12/2002 | Gillis et al. | |
| 2004/0110221 A1 | 6/2004 | Twine et al. | |
| 2004/0175743 A1 | 9/2004 | Burczynski et al. | |

FOREIGN PATENT DOCUMENTS

| | | |
|---|---|---|
| WO | WO00/40749 | 7/2000 |
| WO | WO00/63364 | 10/2000 |
| WO | WO01/81916 | 11/2001 |
| WO | WO02/40000 | 5/2002 |
| WO | WO 02/40717 A2 | 5/2002 |
| WO | WO03/032813 | 4/2003 |
| WO | WO2004/048933 | 6/2004 |
| WO | WO 2004/048933 A2 | 6/2004 |
| WO | WO2004/072265 | 8/2004 |
| WO | WO 2004/072265 A2 | 8/2004 |
| WO | WO 2004/097052 A2 | 11/2004 |

OTHER PUBLICATIONS

Hidalgo et al. "The Rapamycin-Sensitive Signal Transduction pathway as a Target for Cancer Therapy," Oncogene (2000) vol. 19, pp. 6680-6686.*
Panelli et al. "Gene-Expression Profiling of the Response of Peripheral Blood Mononuclear Cells and Melanoma Metastases to Systemic IL-2 Administration," Genome Biology (2002) vol. 3, No. 7, pp. 0035.1-0035.17.*
Wagner, J.A. "Overview of Biomarkers and Surrogate Endpoints in Drug Development," Disease Markers 18(2):41-46, 2002.*
Frank, R. and Hargreaves, R. "Clinical Biomarkers in Drug Discovery," Nature Reviews:Drug Discovery 2:566-580, 2003.*
Feng, Z. et al. "Research Issues and Strategies for Genomic and Proteomic Biomarker Discovery and Validation: A Statistical Perspective," Pharmacogenomics 5(6):709-719, 2004.*
Twine, N.C. et al. "Disease-associated Expression Profiles in Peripheral Blood Mononuclear Cells from Patients with Advanced Renal Cell Carcinoma," Cancer Research 63(18):6069-6075, 2003.*
U.S. Appl. No. 60/427,982, Burczynski et al.
U.S. Appl. No. 60/459,782, Twine et al.
U.S. Appl. No. 60/446,133, Burczynski et al.
U.S. Appl. No. 60/538,246, Burczynski et al.
U.S. Appl. No. 60/466,067, Dorner et al.
A.H. Kibbe, Handbook of Pharmaceutical Excipients, 3rd Edition, Pharmaceutical Press, London, U.K., 2000.
Affymetrix GeneChip® Expression Analysis, Data Analysis Fundamentals.
Affymetrix GeneChip® Expression Analysis Technical Manual.
Armstrong, S. A. et al., MLL translocations specify a distinct gene expression profile that distinguishes a unique leukemia, *Nat. Genet.*, 30(1):41-47, 2002.
Bosma, A. J. et al., Detection of circulating breast tumor cells by differential expression of marker genes, *Clin. Cancer Res.*, 8(6):1871-1877, 2002.
Davis, I. J. et al., Cloning of an *Alpha-TFEB* fusion in renal tumors harboring the t(6;11)(p21;q13) chromosome translocation, *Proc. Natl. Acad. Sci. USA*, 100(10):6051-6056, 2003.
Deprimo, S.E. et al., Expression profiling of blood samples from an SU5416 Phase III metastatic colorectal cancer clinical trial: a novel strategy for biomarker identification, *BMC Cancer*, 3(3):1-12, 2003.
Park, W.Y. et al., Identification of radiation-specific responses from gene expression profile, *Oncogene*, 21(55):8521-8528, 2002.

(Continued)

*Primary Examiner*—Jerry Lin
(74) *Attorney, Agent, or Firm*—Joseph E. Zahner

(57) ABSTRACT

Methods, systems and equipment useful for monitoring in vivo activities of CCI-779 or other drugs. Numerous drug activity genes can be identified by the present invention. The expression profiles of these genes in peripheral blood mononuclear cells are modulatable by CCI-779 or other drugs. Therefore, these genes can be used as surrogate markers for detecting or monitoring drug activities in vivo.

4 Claims, 1 Drawing Sheet

OTHER PUBLICATIONS

Pomeroy, S. L. et al., Supplementary Information for Nature's Paper: Prediction of central nervous system embryonal tumour outcome based on gene expression, pp. 1-104, 2002.

Pomeroy, S. L. et al., Prediction of central nervous system embryonal tumour outcome based on gene expression, *Nature*, 415(6870):436-442, 2002.

Ramaswamy, S. et al., Multiclass cancer diagnosis using tumor gene expression signatures, *Proc. Natl. Acad. Sci. USA*, 98(26):15149-15154, 2001.

Snedecor, G. W. et al., Correlation, In Statistical Methods, Eighth Edition, Chapter 10, pp. 177-195, Iowa State University Press, Ames, Iowa, 1989.

WHO Handbook for Reporting Results of Cancer Treatment, WHO Offset Publication No. 48, pp. 1-45, World Health Organization, Geneva, Switzerland, 1979.

Lichtenfels, R. et al., "Identification of metabolic enzymes in renal cell carcinoma utilizing PROTEOMEX analyses", *Biochimica et Biophysica Acta*, vol. 1646, No. 1-2, Mar. 21, 2003, pp. 21-31.

Peralba, Josep Maria, et al., "Pharmacodynamic Evaluation of the rapamycin ester CCI-779," *Proceedings of the American Association for Cancer Research Annual Meeting*, vol. 43, Mar. 2002 , pp. 1000-1001.

Lockhart, et al., *Nature Biotechnology*, 14: 1675-80 (1996).

Hill, et al., *Science*, 290: 809-812 (2000).

Burczynski et al., "Pharmacogenomic expression profiling of renal cell carcinoma in a phase II trial of CCI-779: identification of surrogate markers of disease and predictors of outcome in the compartment of peripheral blood", *European Journal of Cancer, Pergamon Press*, Oxford, GB, vol. 38, Nov. 2002, p. S51.

Schulze-Koops, H., et al., "Persistent reduction in IL-6 mRNA in peripheral blood mononuclear cells of patients with rheumatoid arthritis after treatment with a monoclonal antibody to CD54 (ICAM-1)," *Clinical and Experimental Immunology*, vol. 106, No. 2, Nov. 1996, pp. 190-196.

Dipaola, R. S., et al., "Phase I clinical and pharmacologic study of 13-cis-retinoic acid, interferon alfa, and pacltaxel in patients with prostate cancer and other advanced malignancies," *Journal of Clinical Oncology: Official Journal of the American Society of Clinical Oncology*, vol. 17, No. 7, Jul. 1999, pp. 2213-2218.

"Product Catalogue", *Affymetrix*, Jan. 2002, p. 1.

Su, A. I., et al., "Molecular classification of human carcinomas by use of gene expression signatures", *Cancer Research*, vol. No. 20, Oct. 15, 2001, pp. 7388-7393.

Elit, Laurie, "CCI-779 Wyeth", *Current Opinion in Investigational Drugs*, vol. 3, No. 8, Aug. 2002, pp. 1249-1253.

Riniger, J. A. et al., "Differential gene expression technologies for identifying surrogate markers of drug efficacy and toxicity", *Drug Discovery Today*, vol. 5, No. 12, Dec. 1, 2000, pp. 560-568.

Peralba, Josep Maria et al., "Pharmacodynamic Evaluation of CCI-779, an Inhibitor of mTOR, in Cancer Patients", *Clinical Cancer Research: An Official Journal of the American Association for Cancer Research*, vol. 9, No. 8, Aug. 1, 2003, pp. 2887-2892.

Su, Andrew I., et al., "Large-scale analysis of the human and mouse transcriptomes," *Proceedings of the National Academy of Sciences of the United States of America*, vol. 99, No. 7, Apr. 2, 2002, pp. 4465-4470.

Cox, *Journal Of The Royal Statistical Society*, Series B 34: 187-220 (1972).

Hill, et al., *Genome Biol.* 2:0055.1-0055.13 (2001).

Motzer, et al., *J. Clin. Oncol.*, 17:2530-2540 (1999).

Pai, et al., *J. Clin. Pharmacol.*, 32:242-247 (1992).

Vijver et al., *The New England Journal Of Medicine*, 347: 1999-2009 (2002).

Eisen, et al., *Proc Nat Acad Sci.*, U.S.A., 95 14863-14868 (1998).

Golub, T.R., et al., *Science*, 286: 531-537 (1999.

Kovacs, et al., *J. Pathol.*, 183: 131-133 (1997).

Slonim, D.K., et al., *Procs. of the Fourth Annual International Conference on Computational Molecular Biology*, Tokyo, Japan, Apr. 8-11, pp. 263-272 (2000).

Office Action dated Oct. 29, 2007, from copending U.S. Appl. No. 10/775,169, filed Feb. 11, 2004 (17 pages).

\* cited by examiner

METHODS FOR MONITORING DRUG ACTIVITIES IN VIVO

This application is a continuation-in-part of U.S. patent application Ser. No. 10/775,169, filed Feb. 11, 2004 and entitled "Methods for Monitoring Drug Activities In Vivo" (by Michael Burczynski, et al.), which claims the benefits of U.S. Provisional Application Ser. No. 60/446,133, filed Feb. 11, 2003, U.S. Provisional Application Ser. No. 60/459,782, filed Apr. 3, 2003, and U.S. Provisional Application Ser. No. 60/538,246, filed Jan. 23, 2004, all of which are incorporated herein by reference in their entireties.

TECHNICAL FIELD

This invention relates to methods, systems and equipment useful for monitoring in vivo activities of CCI-779 or other drugs.

BACKGROUND

CCI-779 is an anti-cancer agent with demonstrated significant inhibitory effects on tumor growth in a number of in vitro and in vivo models. Mechanistically, CCI-779 has been shown to inhibit kinase activity of mTOR (mammalian target of rapamycin), a key protein of phosphoinositide (PI) 3-kinase signal transduction. Inhibition leads to arrest of cells in the G1 phase of the cell cycle; an effect thought to delay the time to tumor progression or time to tumor recurrence. CCI-779 is currently undergoing clinical evaluation to treat patients with renal cell carcinoma (RCC).

SUMMARY OF THE INVENTION

One of the main objectives of clinical pharmacogenomic studies is to identify suitable markers for monitoring in vivo activities of CCI-779 or other drugs. The present invention employs easily-obtained tissues, such as peripheral blood, as surrogate tissues for the detection of in vivo activities of CCI-779 or other drugs.

In one aspect, the present invention provides methods that are useful for detecting or monitoring in vivo activities of CCI-779 or other drugs. The methods include comparing an expression profile of at least one drug activity gene in a peripheral blood sample of a patient of interest to a reference expression profile of the gene. The drug activity gene is differentially expressed in peripheral blood mononuclear cells (PBMCs) of patients who have a non-blood disease and are being treated by a drug therapy, as compared to PBMCs of the patients prior to the drug therapy. In many embodiments, the patient of interest has the same non-blood disease and is being treated by the same drug therapy.

In one embodiment, the drug therapy is an anti-cancer therapy, such as CCI-779 therapy, and the non-blood disease is a solid tumor, such as RCC, prostate cancer, or head/neck cancer.

The peripheral blood samples used in the present invention can be, without limitation, whole blood samples or samples comprising enriched PBMCs. Other peripheral blood samples that include PBMCs can also be employed in the present invention.

The expression profiles of the drug activity genes can be determined by various means, such as quantitative RT-PCR, Northern Blot, in situ hybridization, slot-blotting, nuclease protection assay, nucleic acid arrays, enzyme-linked immunosorbent assays (ELISAs), radioimmunoassay (RIAs), fluorescence-activated cell sorters (FACSs), or Western Blots. In addition, two-dimensional SDS-polyacrylamide gel electrophoresis and other high throughput nucleic acid or protein detection techniques can be used.

In many embodiments, the reference expression profile and the expression profile being compared are prepared using the same or comparable methodology. In one example, the reference expression profile includes an average baseline expression profile of a drug activity gene in peripheral blood samples isolated from reference patient(s) prior to the drug therapy. In another example, the reference expression profile includes an expression profile of a drug activity gene in peripheral blood samples of the patient of interest. The reference expression profile and the expression profile being compared can be obtained from the patient of interest at different time points during the course of therapy.

In another aspect, the present invention provides other methods useful for detecting or monitoring drug activities in vivo. The methods include the steps of comparing an expression profile of at least one drug activity gene in a peripheral blood sample of a patient of interest to a reference expression profile of the drug activity gene, where the patient of interest has a non-blood disease (e.g., RCC or another solid tumor) and is being treated by a drug (e.g., CCI-779), and the differences between expression levels of the drug activity gene in PBMCs of patients at a predetermined stage of treatment with the drug and the respective baseline expression levels are correlated with exposure metrics of the drug in peripheral blood of the patients. In many instances, these patients have the non-blood disease.

In one embodiment, the predetermined stage of treatment is 16-week after initiation of the treatment, and the exposure metrics are $AUC_{sum}$ of CCI-779. In another embodiment, the difference between the expression level at the predetermined stage of treatment and that at baseline is correlated with $AUC_{sum}$ of CCI-779 under Spearman's rank correlation. In many embodiments, the p-value of each drug activity gene for the correlation between expression levels and exposure metrics is no more than 0.01, 0.005, 0.001, or less. In still another embodiment, the drug activity gene is selected from Table 1, such as USP11, U2AF65, FOXM1, B4GALT3, UNK_AL046394, COX6A1, UNK_H98552, ACTN4, UNK_AI147237, DPEP1, UNK_AL022318, TNNT1, SULT2B1, SLC25A11, KIAA0857, CYP11A, SLC19A1, IKBKG, PML, or FARP1. In yet another embodiment, the RNA transcripts of the drug activity gene are capable of hybridizing under stringent conditions to a qualifier selected from Table 1. In a further embodiment, the RNA transcripts of the drug activity gene are capable of hybridizing under stringent conditions to a sequence selected from SEQ ID NOS: 1-20.

In still another aspect, the present invention provides methods useful for identifying drug activity genes. The methods include the steps of detecting expression levels of genes in peripheral blood samples of patients who have a non-blood disease and are being treated by a drug, and identifying genes whose expression levels in the peripheral blood samples are correlated with exposure metrics of the drug in peripheral blood of the patients.

In yet another aspect, the present invention provides other methods useful for identifying drug activity genes. The methods include the steps of detecting expression levels of genes in peripheral blood samples of patients who have a non-blood disease and are at a stage of treatment with a drug, and identifying genes whose expression levels in said peripheral blood samples relative to the corresponding baseline expression levels are correlated with exposure metrics of the drug in the peripheral blood of the patients.

In still yet another aspect, the present invention provides kits useful for detecting in vivo activities of CCI-779 or other drugs. In one embodiment, the kits include one or more polynucleotides, and each polynucleotide can hybridize under stringent or nucleic acid array hybridization conditions to an RNA transcript, or the complement thereof, of a drug activity gene. In another embodiment, the kits include one or more antibodies, and each antibody can bind to a polypeptide encoded by a drug activity gene. The drug activity genes can be selected, without limitation, from Table 1.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description.

BRIEF DESCRIPTION OF THE DRAWINGS

The drawings are provided for illustration, not limitation.

DETAILED DESCRIPTION

Figure 1:
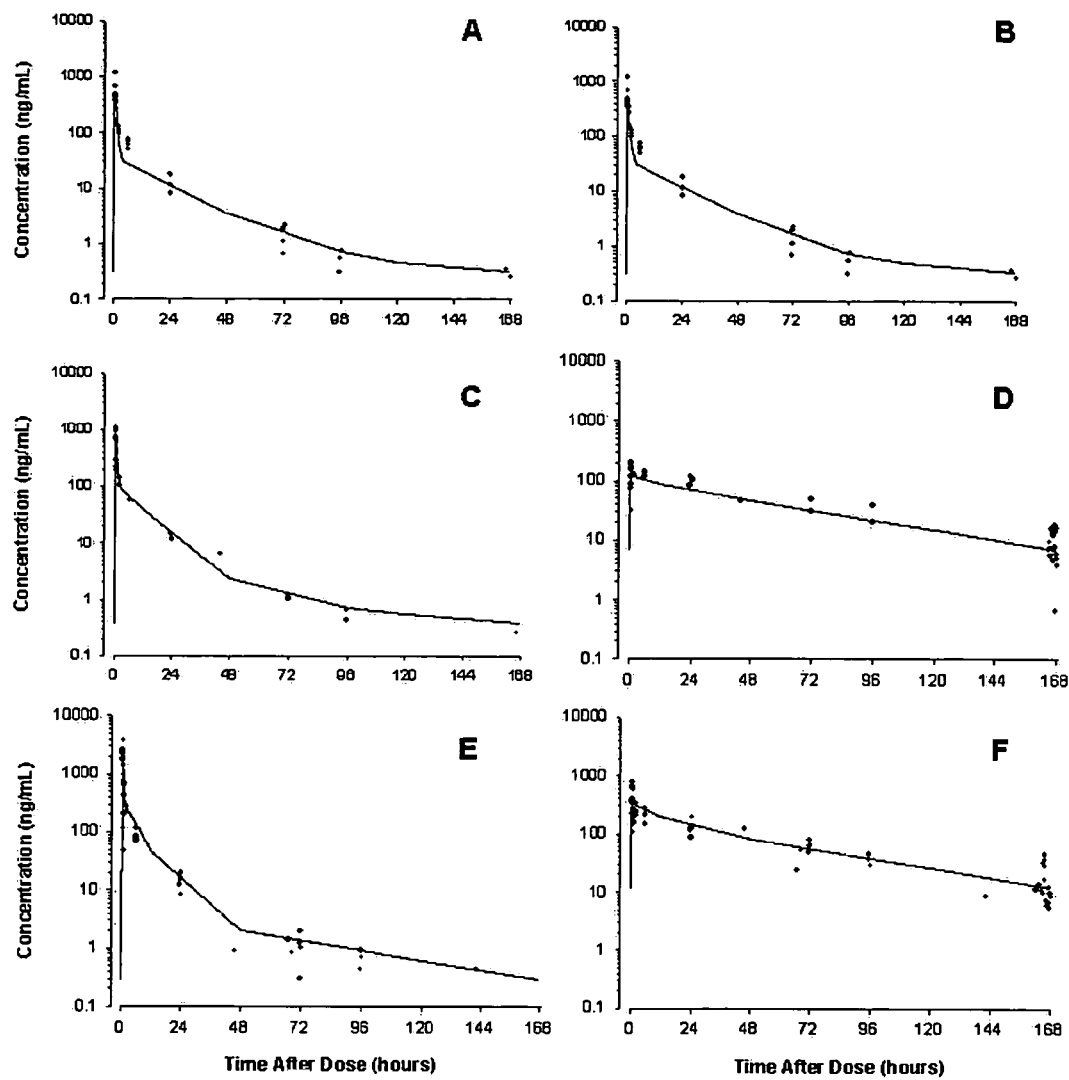
FIG. 1A shows observed (dots) vs. typical patient predicted (line) concentrations of CCI-779 following intravenous 25-mg dose of CCI-779.
FIG. 1B depicts observed (dots) vs. typical patient predicted (line) concentrations of sirolimus following intravenous 25-mg dose of CCI-779.
FIG. 1C demonstrates observed (dots) vs. typical patient predicted (line) concentrations of CCI-779 following intravenous 75-mg dose of CCI-779.
FIG. 1D shows observed (dots) vs. typical patient predicted (line) concentrations of sirolimus following intravenous 75-mg dose of CCI-779.
FIG. 1E illustrates observed (dots) vs. typical patient predicted (line) concentrations of CCI-779 following intravenous 250-mg dose of CCI-779.
FIG. 1F depicts observed (dots) vs. typical patient predicted (line) concentrations of sirolimus following intravenous 250-mg dose of CCI-779.

The present invention provides methods, systems and equipment that are useful for the detection of in vivo activities of CCI-779 or other drugs. Numerous drug activity genes can be identified by the present invention. The expression profiles of these genes in PBMCs are modulatable by CCI-779 or other drugs. Therefore, these genes can be used as surrogate markers for detecting or monitoring drug activities in vivo. In one embodiment, the methods of the present invention include comparing the expression profile of at least one drug activity gene in a peripheral blood sample of a patient of interest to a reference expression profile of the same drug activity gene. The patient of interest has a non-blood disease, such as RCC, prostate cancer, or another solid tumor, and is being treated by a drug therapy. A change in peripheral blood expression profiles of the drug activity gene before and after initiation of the drug therapy is indicative of in vivo drug activities. In many cases, the reference expression profile is determined by using baseline peripheral blood samples isolated from the patent of interest or reference patient(s) prior to the drug therapy. Peripheral blood samples amenable to the present invention include, but are not limited to, whole blood samples or samples comprising enriched PBMCs. Expression profiles of drug activity genes can be detected using a variety of methods, such as quantitative RT-PCT, Northern Blot, in situ hybridization, nucleic acid arrays, enzyme-linked immunosorbent assay (ELISA), radioimmunoassay (RIA), FACS (fluorescence-activated cell sorter), or Western Blot. The drug activity genes of the present invention may also be used for assessing the efficiency of a drug therapy.

Various aspects of the invention are described in further detail in the following sections. The use of sections is not meant to limit the invention. Each section and subsection may apply to any aspect of the invention. In this application, the use of "or" means "and/or" unless stated otherwise. Also, the use of the singular includes the plural unless stated otherwise.

A. GENERAL METHODS FOR IDENTIFYING DRUG ACTIVITY GENES

The availability of the human genome sequence, together with new developments in technology, such as DNA microarrays, proteomics and computational biology, allows systemic gene expression studies for various diseases. The present invention employs the systematic gene expression analysis technique to identify genes whose expression in peripheral blood can be modulated by a therapeutic agent such as CCI-779. These genes are herein referred to as "drug activity genes." The genes whose expression levels in peripheral blood can be modified by CCI-779 are refereed to as "CCI-779 activity genes."

Drug activity genes can be identified by comparing peripheral blood gene expression profiles before and after initiation of a drug treatment. Numerous methods are available for this purpose.

In one embodiment, gene expression profiles are detected by measuring the levels of RNA transcripts in peripheral blood samples. In one example, total RNAs or polyA$^+$ RNAs are isolated from peripheral blood samples using conventional means. The isolated RNAs are amplified to produce cDNAs or cRNAs. Peripheral blood gene expression profiles are then determined by measuring the amount of the amplified cDNAs or cRNAs.

In another embodiment, peripheral blood gene expression profiles are determined by measuring the levels of polypeptides in peripheral blood samples. The amounts of polypeptides in peripheral samples can be detected using various methods, such as ELISAs, RIAs, FACSs, Western Blots, or other immunoassays. In addition, two-dimensional gel electrophoresis/mass spectrometry or other high throughput protein sequencing and identification methods can be used.

In yet another embodiment, nucleic acid arrays are used for detecting or comparing gene expression profiles in peripheral blood samples. Nucleic acid arrays allow for quantitative detection of the expression levels of a large number of genes at one time. Examples of nucleic acid arrays include, but are not limited to, Genechip® microarrays from Affymetrix (Santa Clara, Calif.), cDNA microarrays from Agilent Technologies (Palo Alto, Calif.), and bead arrays described in U.S. Pat. Nos. 6,288,220 and 6,391,562.

The polynucleotides to be hybridized to nucleic acid arrays can be labeled with one or more labeling moieties to allow for detection of hybridized polynucleotide complexes. The labeling moieties can include compositions that are detectable by spectroscopic, photochemical, biochemical, bioelectronic, immunochemical, electrical, optical or chemical means. Exemplary labeling moieties include radioisotopes, chemiluminescent compounds, labeled binding proteins, heavy metal atoms, spectroscopic markers such as fluorescent markers and dyes, magnetic labels, linked enzymes, mass spectrometry tags, spin labels, electron transfer donors and acceptors, and the like. Unlabeled polynucleotides can also be employed. The polynucleotides can be DNA, RNA, or a modified form thereof.

Hybridization reactions can be performed in absolute or differential hybridization formats. In the absolute hybridization format, polynucleotides derived from one sample, such as a peripheral blood sample isolated from a cancer patient at a particular treatment stage, are hybridized to the probes in a nucleic acid array. Signals detected after the formation of hybridization complexes correlate to the polynucleotide levels in the sample. In the differential hybridization format, polynucleotides derived from two biological samples, such as one isolated from a cancer patient at a first stage of treatment and the other isolated from the same patient but at a second stage of treatment, are labeled with different labeling moieties. A mixture of these differently labeled polynucleotides is added to a nucleic acid array. The nucleic acid array is then examined under conditions in which the emissions from the two different labels are individually detectable. In one embodiment, the fluorophores Cy3 and Cy5 (Amersham Pharmacia Biotech, Piscataway N.J.) are used as the labeling moieties for the differential hybridization format.

Signals gathered from nucleic acid arrays can be analyzed using commercially available software, such as those provide by Affymetrix or Agilent Technologies. Controls, such as for scan sensitivity, probe labeling and cDNA/cRNA quantitation, can be included in the hybridization experiments. In many embodiments, the nucleic acid array expression signals are scaled or normalized before being subject to further analysis. For instance, the expression signals for each gene can be normalized to take into account variations in hybridization intensities when more than one array is used under similar test conditions. Signals for individual polynucleotide complex hybridization can also be normalized using the intensities derived from internal normalization controls contained on each array. In addition, genes with relatively consistent expression levels across the samples can be used to normalize the expression levels of other genes. In one embodiment, the expression levels of the genes are normalized across the samples such that the mean is zero and the standard deviation is one. In another embodiment, the expression data detected by nucleic acid arrays are subject to a variation filter which excludes genes showing minimal or insignificant variation across all samples.

A variety of peripheral blood samples can be used in the present invention. In one embodiment, the peripheral blood samples are whole blood samples. In another embodiment, the peripheral blood samples comprise enriched PBMCs. By "enriched," it means that the percentage of PBMCs in the sample is higher than that in whole blood. In many cases, the PBMC percentage in an enriched sample is at least 1, 2, 3, 4, 5 or more times higher than that in whole blood. In many other cases, the PBMC percentage in an enriched sample is at least 90%, 95%, 98%, 99%, 99.5%, or more. Blood samples containing enriched PBMCs can be prepared using any method known in the art, such as Ficoll gradients centrifugation or cell purification tubes (CPTs).

Peripheral blood samples used in the present can be isolated at any stage of a drug treatment (including at baseline before the drug treatment). For instance, the samples can be isolated from patients at 1 day, 2 days, 3 days, 4 days, 5 days, 6 days, 1 week, 2 weeks, 3 weeks, 4 weeks, 8 weeks, or 16 weeks after initiation of the drug treatment. Other time points can also be used.

In many embodiments, the patients from which the peripheral blood samples are isolated have a non-blood disease, such as a solid tumor. Solid tumors amenable to the present invention include, but are not limited, RCC, prostate cancer, head/neck cancer, ovarian cancer, testicular cancer, brain tumor, breast cancer, lung cancer, colon cancer, pancreas cancer, stomach cancer, bladder cancer, skin cancer, cervical cancer, uterine cancer, and liver cancer. In one embodiment, the solid tumors have the following characteristics: (1) a mass of hyperproliferating cells of clonal origin, and (2) acquisition of an aggressively invasive phenotype, where cancer cells leave the tissue of origin and establish new tumor metastases at distant sites. In one example, the patients have RCC.

Any cancer or disease treatment can be evaluated by the present invention. In one embodiment, the cancer treatments include the use of cytokines, such as interferon or interleukin 2. In another embodiment, the cancer treatments include the use of chemotherapy drugs, either individually or in combination with other drugs, cytokines or therapies. Suitable chemotherapy drugs include, but are not limited to, CCI-779, AN-238, vinblastine, floxuridine, 5-fluorouracil, and tamoxifen. AN238 is a cytotoxic agent which has 2-pyrrolinodoxorubicin linked to a somatostatin (SST) carrier octapeptide. AN238 can be targeted to SST receptors on the surface of RCC tumor cells. Moreover, monoclonal antibodies, antiangiogenesis drugs, and anti-growth factor drugs can be employed to treat cancers.

Drug activity genes that are differentially expressed in PBMCs at one stage of treatment relative to another stage of treatment (including baseline) can be identified. In one embodiment, the PBMC expression level of a drug activity gene is substantially higher or lower at one stage of treatment than at another stage of treatment. For instance, an average PBMC expression level of a drug activity gene at one stage of treatment can be at least 0.5, 1, 2, 3, 4, 5, 10, 20, or more times higher than that at another stage of treatment. In another embodiment, the p-value of Student's t-test for the different expression profiles of a drug activity gene at two stages of treatment is no greater than 0.01, 0.005, 0.001, 0.0005, or less.

In yet another embodiment, drug activity genes are identified using statistical tests, such as Spearman's rank correlation. Spearman's rank correlation coefficient has the formula of:

$$r_S = SS_{UV}/(SS_{UU}SS_{VV})^{1/2}$$

where $SS_{UV} = \Sigma U_i V_i - [(\Sigma U_i)(\Sigma V_i)]/n$, $SS_{UU} = \Sigma U_i^2 - [(\Sigma U_i)^2]/n$, and $SS_{VV} = \Sigma U_i^2 - [(\Sigma U_i)^2]/n$. $U_i$ is the expression level ranking of a gene of interest, $V_i$ is the ranking of the clinical outcome, and n represents the number of patients. The shortcut formula for Spearman's rank correlation coefficient is $r_S = 1 - (6 \times \Sigma d_i^2)/[n(n^2-1)]$, where $d_i = U_i - V_i$. The Spearman's test is similar to the Pearson's correlation except that it is based on ranks and is thus more suitable for data that is not normally distributed.

The correlation coefficient for a drug activity gene can be either positive or negative, provided that the correlation is statistically significant. In many embodiments, the p-value for the correlation for each drug activity gene identified by Spearman's rank correlation test is no greater than 0.01, 0.005, 0.001, 0.0005, 0.0001, or less. In many other embodiments, the Spearman correlation coefficient of a drug activity gene has an absolute value of at least 0.3, 0.4, 0.5, 0.6, 0.7, 0.8, 0.9, or more.

B. IDENTIFICATION OF CCI-779 ACTIVITY GENES

In a randomized, double-blind, multicenter trial, once-weekly intravenous doses of 25-, 75-, or 250-mg of CCI-779 were administered to patients with advanced renal cancer that were either previously treated, or untreated and not appropriate candidates for high dose interlukin-2 therapy. Whole blood for CCI-779 and metabolite concentrations was drawn for population pharmacokinetic analysis, and Bayesian-predicted area under the concentration-time curves for parent drug (AUC), parent plus metabolite ($AUC_{sum}$), and cumulative AUC and $AUC_{sum}$ were derived. Additional whole blood samples were collected prior to therapy, at 8 weeks and at 16 weeks post-therapy for the purpose of identifying transcriptional effects in PBMCs from patients treated with CCI-779. RNA samples from CCI-779 treated patient PBMCs were converted to labeled probes and hybridized to oligonucleotide arrays containing over 12,600 human sequences (HgU95A, Affymetrix).

The final population model of CCI-779 and sirolimus (a hydrolysis product of CCI-779 produced in the bodies of patients) included 235 and 305 observations, respectively, from 50 patients. For CCI-779 clearance, factors for dose, attenuation of exposure with multiple-dose, and effect of body surface area were included. For sirolimus, a factor for dose was included. Differences in age, gender, race or renal risk survival factor did not influence drug disposition. Correlation of pharmacokinetic parameters with gene expression revealed a set of transcripts in patient PBMCs with expression levels that were significantly correlated with cumulative $AUC_{sum}$ at 16 weeks post therapy. These transcripts represent biomarkers of CCI-779 exposure in the surrogate tissue of peripheral blood.

Examples of the transcripts thus identified are listed in Table 1. Each transcript is defined by a qualifier on HgU95A. Each qualifier corresponds to at least one CCI-779 activity gene, and the RNA transcripts of the gene can hybridize under stringent or nucleic acid array hybridization conditions to the qualifier. As used herein, "hybridize to a qualifier" means to hybridize to at least one oligonucleotide probe of the qualifier. In many cases, the RNA transcripts of a CCI-779 activity gene can hybridize under stringent or nucleic acid array hybridization conditions to at least 2, 4, 6, 8, 10, 12, 14, 16 or more oligonucleotide probes of the corresponding qualifier. The sequences for the oligonucleotide probes of each qualifier can be readily obtained from Affymetrix. Table 1 also provides the gene names for each drug activity gene. Detailed information of these drug activity genes is further described in Table 2.

TABLE 1

Examples of CCI-779 Activity Genes with Alterations in PBMC Expression that Are Correlated with Cumulative Exposure Metrics

| Qualifier | Gene Name | Accession No | Reference Seq |
|---|---|---|---|
| 162_at | USP11 | U44839 | SEQ ID NO: 1 |
| 32557_at | U2AF65 | AI762438 | SEQ ID NO: 2 |
| 41324_g_at | FOXM1 | U90917 | SEQ ID NO: 3 |
| 39445_at | B4GALT3 | AF038661 | SEQ ID NO: 4 |
| 39868_at | UNK_AL046394 | AL046394 | SEQ ID NO: 5 |
| 41206_r_at | COX6A1 | AI540925 | SEQ ID NO: 6 |
| 39103_s_at | UNK_H98552 | H98552 | SEQ ID NO: 7 |
| 41753_at | ACTN4 | U48734 | SEQ ID NO: 8 |
| 34104_i_at | UNK_AI147237 | AI147237 | SEQ ID NO: 9 |
| 36114_r_at | TNNT1 | M19309 | SEQ ID NO: 10 |
| 37413_at | DPEP1 | J05257 | SEQ ID NO: 11 |
| 37939_at | UNK_AL022318 | AL022318 | SEQ ID NO: 12 |
| 41034_s_at | SULT2B1 | U92315 | SEQ ID NO: 13 |
| 32197_at | SLC25A11 | AF070548 | SEQ ID NO: 14 |
| 33882_at | KIAA0857 | AB020664 | SEQ ID NO: 15 |
| 37195_at | CYP11A | M14565 | SEQ ID NO: 16 |

TABLE 1-continued

Examples of CCI-779 Activity Genes with Alterations in PBMC Expression that Are Correlated with Cumulative Exposure Metrics

| Qualifier | Gene Name | Accession No | Reference Seq |
|---|---|---|---|
| 33135_at | SLC19A1 | U17566 | SEQ ID NO: 17 |
| 36004_at | IKBKG | AF074382 | SEQ ID NO: 18 |
| 567_s_at | PML | M79463 | SEQ ID NO: 19 |
| 32148_at | FARP1 | AI701049 | SEQ ID NO: 20 |

Each qualifier in Table 1 also has a reference sequence from which the oligonucleotide probes of the qualifier can be derived. These reference sequences are depicted in SEQ ID NOS:1-20, respectively. In general, each "n" position in a reference sequence represents at least one nucleotide selected from a, t, g, and c, or contains no nucleotide residue. In many instances, the RNA transcripts of a drug activity gene, or the complements thereof, can hybridize under stringent conditions to a reference sequence of the qualifier that corresponds to the drug activity gene. As used herein, a polynucleotide can hybridize to a reference sequence if the polynucleotide can hydride to an unambiguous fragment of the reference sequence, where the unambiguous fragment includes at least 25 consecutive nucleotide residues.

In addition, each qualifier or drug activity gene in Table 1 has an Entrez nucleotide sequence database accession number ("Accession No"). The Entrez nucleotide sequence database is maintained by the National Center of Biotechnology Information (NCBI), National Library of Medicine, Washington, D.C. The database collects sequences from several sources, including GenBank, RefSeq, and PDB.

TABLE 2

Examples of CCI-779 Activity Genes

| Gene Name | Gene Title | Unigene Accession |
|---|---|---|
| USP11 | ubiquitin specific protease 11 | Hs.171501 |
| U2AF65 | U2 small nuclear ribonucleoprotein auxiliary factor (65 kD) | Hs.7655 |
| FOXM1 | forkhead box M1 | Hs.239 |
| B4GALT3 | UDP-Gal: betaGlcNAc beta 1,4-galactosyltransferase, polypeptide 3 | Hs.321231 |
| UNK_AL046394 | Cluster Incl AL046394: DKFZp434M217_r1 434 (synonym: htes3) *Homo sapiens* cDNA clone DKFZp434M217 5', mRNA sequence. | Hs.121241 |
| COX6A1 | cytochrome c oxidase subunit VIa polypeptide 1 | Hs.180714 |
| UNK_H98552 | *Homo sapiens* mRNA; cDNA DKFZp586I0523 (from clone DKFZp586I0523) | Hs.308467 |
| ACTN4 | actinin, alpha 4 | Hs.182485 |
| UNK_AI147237 | *Homo sapiens* isolate RP immunoglobulin heavy chain FW2-JH region gene, partial cds | Hs.300697 |
| TNNT1 | troponin T1, skeletal, slow | Hs.73980 |
| DPEP1 | dipeptidase 1 (renal) | Hs.109 |
| UNK_AL022318 | Human DNA sequence from clone 150C2 on chromosome 22q13.1-13.2. Contains the gene for Phorbolin 3, a novel gene and up to nine novel genes and pseudogenes for proteins similar to Phorbolin and APOBEC1 (Apolipoprotein B mRNA editing protein. Contains ESTs STSs and GSSs | |
| SULT2B1 | sulfotransferase family 2B, member 1 | Hs.94581 |
| SLC25A11 | solute carrier family 25 (mitochondrial carrier; oxoglutarate carrier), member 11 | Hs.184877 |

TABLE 2-continued

Examples of CCI-779 Activity Genes

| Gene Name | Gene Title | Unigene Accession |
|---|---|---|
| KIAA0857 | KIAA0857 protein | Hs.24557 |
| CYP11A | cytochrome P450, subfamily XIA (cholesterol side chain cleavage) | Hs.76205 |
| SLC19A1 | solute carrier family 19 (folate transporter), member 1 | Hs.84190 |
| IKBKG | inhibitor of kappa light polypeptide gene enhancer in B-cells, kinase gamma | Hs.43505 |
| PML | promyelocytic leukemia | Hs.89633 |
| FARP1 | FERM, RhoGEF (ARHGEF) and pleckstrin domain protein 1 (chondrocyte-derived) | Hs.183738 |

The biological mechanisms underlying the CCI-779 modulation of the expression levels of the CCI-779 activity genes have yet to be elucidated. Without being limited to any specific theory, the modulation may be attributed to the direct effect of CCI-779 on PBMCs or other blood cells. It may also be caused by the effect of CCI-779 on renal cell carcinoma tumors, which in turn induce the change of the gene expression profile in the peripheral blood cells.

As appreciated by those skilled in the art, the above-described methodology can be employed to identify genes whose expression profiles in PBMCs can be modulated by other drugs.

C. DETECTING AND MONITORING IN VIVO DRUG ACTIVITIES

The CCI-779 activity genes identified in the present invention can be used to detect or monitor CCI-779 drug activities in patients who receive a CCI-779 treatment. Peripheral blood samples can be isolated at different stages of the CCI-779 treatment. The expression profile of one or more CCI-779 activity genes in the peripheral blood samples is determined and compared to a reference expression profile (e.g., the baseline expression profile prior to the treatment). A significant change in the gene expression profiles indicates in vivo activities of CCI-779. The detection of CCI-779 drug activities can be qualitative or quantitative. In vivo activities of other drugs can be similarly detected or monitored using respective drug activity genes, as appreciated by those skilled in the art.

In many embodiments, the expression profiles of drug activity genes are determined by measuring the levels of RNA transcripts of these genes. Suitable methods for this purpose include, but are not limited to, RT-PCT, Northern Blot, in situ hybridization, slot-blotting, nuclease protection assay, and nucleic acid arrays. The peripheral blood samples can be, without limitation, whole blood samples or samples containing enriched PBMCs.

In one embodiment, RNA isolated from peripheral blood samples is first amplified to cDNA or cRNA. The amplification can be specific or non-specific. Suitable amplification methods include, but are not limited to, reverse transcriptase PCR, isothermal amplification, ligase chain reaction, and Qbeta replicase. The amplified nucleic acid products can be detected or quantitated through hybridization to probes which can be directly or indirectly labeled.

Amplification primers and hybridization probes for a drug activity gene can be prepared from the gene sequence by using any method known in the art. Gene sequences suitable for this purpose include, but are not limited to, exons, introns, or the 3' or 5' untranslated regions, or any combination thereof. In one embodiment, probes/primers are designed based on the sequence in or near the 3' protein-coding region of a drug activity gene. For instance, the nucleotide sequence encoding the last 100 to 300 amino acid residues in the C-terminus region of the drug activity gene product can be selected to design probes or primers. Where a drug activity gene is a hypothetical or putative gene whose expression is supported only by EST or mRNA data, or where the genomic location(s) of a drug activity gene has not been determined or the gene may correspond to multiple genomic loci, the probes/primers for the gene can be designed based on the reference sequence or oligonucleotide probes of the corresponding qualifier, or the sequence under the corresponding Entrez accession number.

The length of the probes/primers can be selected to achieve the desired hybridization or amplification effect. For instance, each probe can comprise at least 15, 20, 25, 50, 75, 100, 125, 150, 175, 200, 225, 250, 275, 300, 325, 350, 400 or more nucleotides. In one embodiment, each probe/primer has relatively high sequence complexity and does not have any ambiguous residue (i.e., "n" residues).

In many embodiments, the probes/primers for a gene can hybridize under stringent or highly stringent conditions to the RNA transcripts, or the complements thereof, of the gene. As used herein, "stringent conditions" are at least as stringent as, for example, conditions G-L shown in Table 7. "Highly stringent conditions" are at least as stringent as conditions A-F shown in Table 7. As used in Table 7, hybridization is carried out under the hybridization conditions (Hybridization Temperature and Buffer) for about four hours, followed by two 20-minute washes under the corresponding wash conditions (Wash Temp. and Buffer).

TABLE 7

Stringency Conditions

| Stringency Condition | Polynucleotide Hybrid | Hybrid Length (bp)[1] | Hybridization Temperature and Buffer[H] | Wash Temp. and Buffer[H] |
|---|---|---|---|---|
| A | DNA:DNA | >50 | 65° C.; 1xSSC -or- 42° C.; 1xSSC, 50% formamide | 65° C.; 0.3xSSC |
| B | DNA:DNA | <50 | $T_B^*$; 1xSSC | $T_B^*$; 1xSSC |
| C | DNA:RNA | >50 | 67° C.; 1xSSC -or- 45° C.; 1xSSC, 50% formamide | 67° C.; 0.3xSSC |
| D | DNA:RNA | <50 | $T_D^*$; 1xSSC | $T_D^*$; 1xSSC |
| E | RNA:RNA | >50 | 70° C.; 1xSSC -or- 50° C.; 1xSSC, 50% formamide | 70° C.; 0.3xSSC |
| F | RNA:RNA | <50 | $T_F^*$; 1xSSC | $T_F^*$; 1xSSC |

TABLE 7-continued

Stringency Conditions

| Stringency Condition | Polynucleotide Hybrid | Hybrid Length (bp)[1] | Hybridization Temperature and Buffer[H] | Wash Temp. and Buffer[H] |
|---|---|---|---|---|
| G | DNA:DNA | >50 | 65° C.; 4xSSC -or- 42° C.; 4xSSC, 50% formamide | 65° C.; 1xSSC |
| H | DNA:DNA | <50 | $T_H$*; 4xSSC | $T_H$*; 4xSSC |
| I | DNA:RNA | >50 | 67° C.; 4xSSC -or- 45° C.; 4xSSC, 50% formamide | 67° C.; 1xSSC |
| J | DNA:RNA | <50 | $T_J$*; 4xSSC | $T_J$*; 4xSSC |
| K | RNA:RNA | >50 | 70° C.; 4xSSC -or- 50° C.; 4xSSC, 50% formamide | 67° C.; 1xSSC |
| L | RNA:RNA | <50 | $T_L$*; 2xSSC | $T_L$*; 2xSSC |

[1]The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[H]SSPE (1xSSPE is 0.15 M NaCl, 10 mM NaH$_2$PO$_4$, and 1.25 mM EDTA, pH 7.4) can be substituted for SSC (1xSSC is 0.15 M NaCl and 15 mM sodium citrate) in the hybridization and wash buffers.
$T_B$* - $T_R$*: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6($\log_{10}$Na$^+$) + 0.41(% G + C) − (600/N), where N is the number of bases in the hybrid, and Na$^+$ is the molar concentration of sodium ions in the hybridization buffer (Na$^+$ for 1xSSC = 0.165 M).

In one embodiment, the probes/primers for a drug activity gene are selected from regions which significantly diverge from the sequences of other genes. Such regions can be determined by checking the probe/primer sequences against a human genome sequence database, such as the Entrez database at the NCBI. One algorithm suitable for this purpose is the BLAST algorithm. This algorithm involves first identifying high scoring sequence pairs (HSPs) by identifying short words of length W in the query sequence, which either match or satisfy some positive valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence to increase the cumulative alignment score. Cumulative scores are calculated using, for nucleotide sequences, the parameters M (reward score for a pair of matching residues; always >0) and N (penalty score for mismatching residues; always <0). The BLAST algorithm parameters W, T, and X determine the sensitivity and speed of the alignment. These parameters can be adjusted for different purposes, as appreciated by one of ordinary skill in the art.

In one embodiment, quantitative RT-PCR (such as Taq-Man, ABI) is used for detecting and comparing the peripheral blood expression profiles of drug activity genes. Quantitative RT-PCR involves reverse transcription (RT) of RNA to cDNA followed by relative quantitative PCR (RT-PCR).

In PCR, the number of molecules of the amplified target DNA increases by a factor approaching two with every cycle of the reaction until some reagent becomes limiting. Thereafter, the rate of amplification becomes increasingly diminished until there is not an increase in the amplified target between cycles. If one plots a graph on which the cycle number is on the X axis and the log of the concentration of the amplified target DNA is on the Y axis, one observes that a curved line of characteristic shape is formed by connecting the plotted points. Beginning with the first cycle, the slope of the line is positive and constant. This is said to be the linear portion of the curve. After some reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR is proportional to the starting concentration of the target before the PCR was begun. By determining the concentration of the PCR products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived may be determined for the respective tissues or cells. This direct proportionality between the concentration of the PCR products and the relative mRNA abundances is true in the linear range portion of the PCR reaction.

The final concentration of the target DNA in the plateau portion of the curve is determined by the availability of reagents in the reaction mix and is independent of the original concentration of target DNA. Therefore, the sampling and quantifying of the amplified PCR products can be carried out when the PCR reactions are in the linear portion of their curves. In addition, relative concentrations of the amplifiable cDNAs can be normalized to some independent standard, which may be based on either internally existing RNA species or externally introduced RNA species. The abundance of a particular mRNA species may also be determined relative to the average abundance of all mRNA species in the sample.

In one embodiment, the PCR amplification utilizes internal PCR standards that are approximately as abundant as the target. This strategy is effective if the products of the PCR amplifications are sampled during their linear phases. If the products are sampled when the reactions are approaching the plateau phase, then the less abundant product may become relatively over-represented. Comparisons of relative abundances made for many different RNA samples, such as is the case when examining RNA samples for differential expression, may become distorted in such a way as to make differences in relative abundances of RNAs appear less than they actually are. This can be improved if the internal standard is much more abundant than the target. If the internal standard is more abundant than the target, then direct linear comparisons may be made between RNA samples.

A problem inherent in clinical samples is that they are of variable quantity or quality. This problem can be overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5-100 times higher than the mRNA encoding the target. This assay measures relative abundance, not absolute abundance of the respective mRNA species.

In another embodiment, the relative quantitative RT-PCR uses an external standard protocol. Under this protocol, the PCR products are sampled in the linear portion of their amplification curves. The number of PCR cycles that are optimal for sampling can be empirically determined for each target cDNA fragment. In addition, the reverse transcriptase products of each RNA population isolated from the various samples can be normalized for equal concentrations of amplifiable cDNAs. While empirical determination of the linear range of the amplification curve and normalization of cDNA preparations are tedious and time-consuming processes, the resulting RT-PCR assays may, in certain cases, be superior to those derived from a relative quantitative RT-PCR with an internal standard.

Nucleic acid arrays can also be used to detect and compare the expression patterns of drug activity genes in peripheral blood samples isolated at different drug treatment stages. Probes suitable for detecting drug activity genes can be stably attached to known discrete regions on a support substrate. These probes maintain their positions relative to the respective discrete regions during hybridization and subsequent washes. Construction of nucleic acid arrays is well known in the art. Suitable substrates for making nucleic acid arrays include, but are not limited to, glasses, silica, ceramics, nylons, quartz wafers, gels, metals, papers, beads, tubes, fibers, films, membranes, column matrixes, or microtiter plate wells.

A nucleic acid array of the present invention can comprise at least 2, 5, 10, 15, 20, 25, 30, 35, 40, 45, 50, 60, 70, 80, 90, 100, 150, 200, 250, or more different polynucleotide probes, each of which is capable of hybridizing under stringent or nucleic acid array hybridization conditions to the RNA transcripts, or the complements thereof, of a different respective drug activity gene. Multiple probes for the same gene can be used on a single nucleic acid array. The probe density on the array can be in any range. For instance, the density may be 50, 100, 200, 300, 400, 500, or more probes/cm$^2$.

In one embodiment, a substantial portion of all polynucleotide probes on a nucleic acid array of the present invention are probes for CCI-779 or other drug activity genes. For instance, at least 10%, 20%, 30%, 40%, 50%, or more of all probes on the nucleic acid array can hybridize under stringent or nucleic acid array hybridization conditions to the RNA transcripts, or the complements thereof, of drug activity genes.

In another embodiment, nuclease protection assays are used to quantify RNAs derived from the peripheral blood samples. There are many different versions of nuclease protection assays. The common characteristic of these nuclease protection assays is that they involve hybridization of an antisense nucleic acid with the RNA to be quantified. The resulting hybrid double-stranded molecule is then treated with a nuclease which digests single-stranded nucleic acids more efficiently than double-stranded molecules. The amount of antisense nucleic acid that survives digestion is a measure of the amount of the target RNA species to be quantified. An example of nuclease protection assays is the RNase protection assay manufactured by Ambion, Inc. (Austin, Tex.).

In many other embodiments, the peripheral blood expression profiles of drug activity genes are determined by measuring the levels of polypeptides encoded by the genes. Methods suitable for this purpose include, but are not limited to, immunoassays. Examples of suitable immunoassay formats include, but are not limited to, latex or other particle agglutination, electrochemiluminescence, ELISAs, RIAs, sandwich or immunometric assays, time-resolved fluorescence, lateral flow assays, fluorescence polarization, flow cytometry, immunohistochemical assays, dot blots, Western blots, antibody-based radioimaging, and proteomic chips. Other methods such as 2-dimensional SDS-polyacrylamide gel electrophoresis can also be used.

One exemplary method suitable for detecting the levels of target proteins in peripheral blood samples is ELISA. In an exemplifying ELISA, antibodies capable of binding to the target proteins encoded by one or more drug activity genes are immobilized onto a selected surface exhibiting protein affinity, such as wells in a polystyrene or polyvinylchloride microtiter plate. Then, peripheral blood samples to be tested are added to the wells. After binding and washing to remove non-specifically bound immunocomplexes, the bound antigen(s) can be detected. Detection can be achieved by the addition of a second antibody which is specific for the target proteins and is linked to a detectable label. Detection may also be achieved by the addition of a second antibody, followed by the addition of a third antibody that has binding affinity for the second antibody, with the third antibody being linked to a detectable label. Before being added to the microtiter plate, cells in the peripheral blood samples can be lysed using various methods known in the art. Proper extraction procedures can be used to separate the target proteins from potentially interfering substances.

In another exemplifying ELISA, the peripheral blood samples suspected of containing the target proteins are immobilized onto the well surface and then contacted with the antibodies of the invention. After binding and washing to remove non-specifically bound immunocomplexes, the bound antigen is detected. Where the initial antibodies are linked to a detectable label, the immunocomplexes can be detected directly. The immunocomplexes can also be detected using a second antibody that has binding affinity for the first antibody, with the second antibody being linked to a detectable label.

Another exemplary ELISA involves the use of antibody competition in the detection. In this ELISA, the target proteins are immobilized on the well surface. The labeled antibodies are added to the well, allowed to bind to the target proteins, and detected by means of their labels. The amount of the target proteins in an unknown sample is then determined by mixing the sample with the labeled antibodies before or during incubation with coated wells. The presence of the target proteins in the unknown sample acts to reduce the amount of antibody available for binding to the well and thus reduces the ultimate signal.

Different ELISA formats can have certain features in common, such as coating, incubating or binding, washing to remove non-specifically bound species, and detecting the bound immunocomplexes. For instance, in coating a plate with either antigen or antibody, the wells of the plate can be incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test samples. Examples of these nonspecific proteins include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means can also be used. After binding of a protein or antibody to the well, coating with a non-reactive material to reduce background, and washing to remove unbound material, the immobilizing surface is contacted with the control or clinical or biological sample to be tested under conditions effective to allow immunocomplex (antigen/antibody) formation. These conditions may include, for example, diluting the antigens and antibodies with solutions such as BSA, bovine gamma globulin (BGG) and phosphate buffered saline (PBS)/Tween and incubating the antibodies and antigens at room temperature for about 1 to 4 hours or at 4° C. overnight. Detection of the immunocomplex then requires a labeled secondary binding ligand or antibody, or a secondary binding ligand or antibody in conjunction with a labeled tertiary antibody or third binding ligand.

Following all incubation steps in an ELISA, the contacted surface can be washed so as to remove non-complexed material. For instance, the surface may be washed with a solution such as PBS/Tween, or borate buffer. Following the formation of specific immunocomplexes between the test sample and the originally bound material, and subsequent washing, the occurrence of the amount of immunocomplexes can be determined.

To provide a detection means, the second or third antibody can have an associated label. In one embodiment, the label is an enzyme that generates color development upon incubating with an appropriate chromogenic substrate. Thus, for example, one may contact and incubate the first or second immunocomplex with a urease, glucose oxidase, alkaline phosphatase or hydrogen peroxidase-conjugated antibody for a period of time and under conditions that favor the development of further immunocomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl)-benzthiazoline-6-sulfonic acid (ABTS) and $H_2O_2$, in the case of peroxidase as the enzyme label. Quantitation can be achieved by measuring the degree of color generation, e.g., using a spectrophotometer.

Another method suitable for this invention is RIA (radioimmunoassay). An exemplary RIA is based on the competition between radiolabeled-polypeptides and unlabeled polypeptides for binding to a limited quantity of antibodies. Suitable radiolabels include, but are not limited to, $I^{125}$. In one embodiment, a fixed concentration of $I^{125}$-labeled polypeptide is incubated with a series of dilution of an antibody specific to the polypeptide. When the unlabeled polypeptide is added to the system, the amount of the $I^{125}$-polypeptide that binds to the antibody is decreased. A standard curve can therefore be constructed to represent the amount of antibody-bound $I^{125}$-polypeptide as a function of the concentration of the unlabeled polypeptide. From this standard curve, the concentration of the polypeptide in unknown samples can be determined.

Suitable antibodies for this invention include, but are not limited to, polyclonal antibodies, monoclonal antibodies, chimeric antibodies, humanized antibodies, single chain antibodies, Fab fragments, or fragments produced by a Fab expression library. Methods for making these antibodies are well known in the art.

In one embodiment, the antibodies of the present invention can bind to the corresponding drug activity gene products or other desired antigens with a binding affinity constant $K_a$ of at least $10^4 M^{-1}$, $10^5 M^{-1}$, $10^6 M^{-1}$, $10^7 M^{-1}$, $10^8 M^{-1}$, or more.

The antibodies of this invention can be labeled, directly or indirectly, with one or more detectable moieties to allow for detection of antibody-antigen complexes. The detectable moieties can include compositions detectable by spectroscopic, enzymatic, photochemical, biochemical, bioelectronic, immunochemical, electrical, optical or chemical means. The detectable moieties include, but are not limited to, radioisotopes, chemiluminescent compounds, labeled binding proteins, heavy metal atoms, spectroscopic markers such as fluorescent markers and dyes, magnetic labels, linked enzymes, mass spectrometry tags, spin labels, electron transfer donors and acceptors, and the like.

In another embodiment, the levels of polypeptides in peripheral blood samples can be determined by detecting the biological activities associated with the polypeptides. If a biological function/activity of a polypeptide is known or determinable, suitable in vitro assays can be designed to evaluate the biological function/activity, which in turn can be used to determine the amount of the polypeptide in the sample.

Comparison between the expression profile of a patient of interest and a reference expression profile can be conducted manually or electronically. In one embodiment, the reference expression profile is a baseline expression profile representing gene expression in one or more peripheral blood samples isolated prior to a drug treatment. In another embodiment, the reference profile is an expression profile in peripheral blood sample(s) isolated after initiation of the drug treatment. The reference expression profile can be determine using sample(s) isolated from the patient of interest or other reference patient or patients. In many embodiments, the process or methodology that is used to determine the reference expression profile and the expression profile being compared is identical or comparable.

In one example, comparison is carried out by comparing each component in the expression profile of the patient of interest to the corresponding component in the reference expression profile(s). The component can be the expression level of a drug activity gene, a ratio between the expression levels of two drug activity genes, or another measure capable of representing gene expression patterns. The expression level of a gene can be an absolute level, or a normalized or relative level. The difference between two corresponding components can be assessed by fold changes, absolute differences, or other suitable means.

Comparison between expression profiles can also be conducted using pattern recognition or comparison programs. In addition, the serial analysis of gene expression (SAGE) technology, the GEMTOOLS gene expression analysis program (Incyte Pharmaceuticals), the GeneCalling and Quantitative Expression Analysis technology (Curagen), and other suitable methods, programs or systems can be used.

Multiple drug activity genes can be used in the comparison of expression profiles. For instance, 2, 4, 6, 8, 10, 12, 14, 16, 18, 20, 30, 40, 50, or more drug activity genes can be used.

In one embodiment, the drug activity gene(s) used in the comparison can be selected to have relatively small p-values or large differential expression ratios. In one example, the drug activity genes used in the comparison have p-values (e.g., under Student's t-test or an ANOVA analysis) of no greater than 0.01, 0.001, 0.0005, 0.0001, or less. In another example, the expression level of a drug activity gene during a drug treatment increases or decreases by at least 2-fold, 3-fold, 4-fold, 5-fold, or more over the baseline expression level.

In another embodiment, the change in expression level of a drug activity gene from baseline is correlated with an exposure metric (e.g., concentration, AUC, or $AUC_{sum}$) of the drug in peripheral blood samples. Thus, if the expression level change in a patient of interest is similar to that in a control patient whose drug exposure metric is known or determinable, the drug exposure metric in the patient of interest can therefore be predicted.

In yet another embodiment, comparison of the expression profiles is performed electronically, such as by using a computer system. The computer system includes a processor coupled to a memory or storage medium which stores data representing the expression profiles being compared. In one example, the memory or storage medium is readable or rewritable. The stored expression data can be changed, retrieved, or otherwise manipulated. The memory can also store one or more programs capable of causing the processor to compare the expression profiles. In one embodiment, the processor is coupled to a nucleic acid array scanner which sends signals to the processor for analysis.

The materials for use in the methods of the present invention can be included in a kit. The kit can comprise one or more container means such as vials, tubes, or the like, each of the container means comprising one of the elements to be used in a method of the present invention. In one embodiment, one of the container means includes a polynucleotide probe for a drug activity gene of the present invention. The probe can be either labeled or unlabeled. Unlabeled probes can be used in combination with other labeled molecules that are reactive with the unlabeled probe. In another embodiment, one of the container means includes an antibody specific for the polypeptide encoded by a drug activity gene. The antibody can be labeled or unlabeled. In one example, unlabeled antibodies are used in combination with other labeled antibodies, such as second antibodies that are specific for the immunoglobulin constant regions. The kit can also have containers containing buffers, stabilizing agents, biocides, inert proteins, or reporter means. In addition, the kit can include reagents for conducting positive or negative controls. Instructions on how to use the kit can also be included.

It should be understood that the above-described embodiments and the following examples are given by way of illustration, not limitation. Various changes and modifications within the scope of the present invention will become apparent to those skilled in the art from the present description.

E. EXAMPLES

Example 1

Study Design

The following examples evaluated the pharmacogenomic effects of CCI-779 as measured in the surrogate tissue of peripheral blood in RCC patients. The use of microarrays in clinical settings has received increased attention in the clinical and regulatory communities and expression profiles of tumor tissues have identified transcriptional patterns associated with disease, disease severity and even clinical responsiveness. However, access to biopsies is often impractical in clinical settings and in the case of advanced renal cell carcinoma, most patients entering the phase 2 trial had already undergone complete or partial nephrectomy. Because of its clinical accessibility, peripheral blood represents an attractive alternative tissue source (surrogate tissue) for the identification of markers of drug exposure. U.S. Provisional Application Ser. No. 60/459,782, filed Apr. 3, 2003 and entitled "Methods for Diagnosing RCC and/or Solid Tumors" (by Natalie C. Twine, et al.), identified disease-associated transcripts in PBMCs collected from RCC patients prior to the initiation of therapy in the present clinical trial. The following studies identified transcripts in PBMCs that, following initiation of CCI-779 therapy, exhibit temporal profiles correlated with pharmacokinetic measures of CCI-779 exposure in vivo.

The pharmacokinetics of CCI-779 is being studied in patients with cancer receiving CCI-779 either alone or in combination with other chemotherapeutic agents following intravenous administration. Intravenous dosage schedules previously investigated include a cyclical schedule (daily for 5 days every two weeks) and a once-weekly regimen. Exposure in whole blood generally increases less than proportionally with dose. Steady-state volume of distribution ($Vd_{ss}$) is large, increases with dose, and ranges from 230 L (following a 25-mg dose) to as high as 900 L (following a 250-mg dose). Distribution of CCI-779 into red blood cells appears to be preferential at lower doses. Metabolism of CCI-779 occurs mainly via oxidative hydrolysis to form sirolimus. Both CCI-779 and sirolimus are also extensively metabolized via CYP3A enzymes to form various demethylated and hydroxylated isomeric products that are predominantly excreted in the feces. As observed with $Vd_{ss}$, clearance from whole blood also increases with increasing dose with mean values ranging from approximately 20 L/h following a 25-mg dose to 100 L/h following a 250-mg dose (coefficient of variation ~16 to 27%). Terminal half-life of CCI-779 is approximately 14 hours for CCI-779, and 60 to 70 hours for sirolimus metabolite. The following examples evaluated the safety, efficacy, and pharmacokinetic/pharmacodynamic relationship to clinical response of three doses of CCI-779, when administered to patients with advanced, refractory renal cell cancer (RCC).

The following examples were based on a randomized, double-blind, multicenter, outpatient phase 2 study of CCI-779 administered by 30 minute intravenous infusion (via an automatic dispensing pump) in patients with advanced RCC. Eligible patients were randomly assigned to treatment in a 1:1:1 ratio to receive 25 mg, 75 mg, or 250 mg of CCI-779 weekly until evidence of disease progression.

Full pharmacokinetic profiling was planned in a subset of patients, with remaining patients to provide sparse sampling. Time points for whole blood concentrations of CCI-779 and sirolimus in fully sampled patients were scheduled at 0 (predose), 0.5, 1, 2, 6, 24, 74, 96, and 168 hours after the start of the 30 minute infusion during Weeks 1 and 4 of treatment. For patients undergoing limited blood sampling, whole blood was drawn for CCI-779 and sirolimus at 0 (predose), 0.5 hr and at the discretion of the investigator and patient, on one other day following dose during Week 4.

Consent for the pharmacogenomic portion of the clinical study was received and the project was approved by the local Institutional Review Boards at the participating clinical sites.

Blood samples for pharmacogenomic characterization were drawn into cell purification tubes (CPT, Becton Dickinson) prior to therapy and following approximately 8 and 16 weeks of treatment. All blood samples were shipped overnight to the Wyeth Department of Molecular Medicine in Andover, Mass., and PBMCs were isolated from the whole blood samples (8 mL) in CPT tubes according to the manufacturer's procedure.

Example 2

Analytical Methods

The bioanalytical method for CCI-779 was performed using whole blood in a liquid chromatography/tandem mass spectrometry (LC/MS/MS) procedure with deuterated internal standard. Plasma was not used as the matrix of choice due to potential limitations in analyte stability. The method was validated through the quantitation range of 0.25 to 100 ng/mL using 1 mL of EDTA-treated whole blood, and during validation, exhibited inter- and intra-day variabilities $\leq$5% coefficient of variation (CV), and biases $\leq$9.4%. The bioanalytical method for sirolimus also employed an LC/MS/MS procedure that was validated through the quantitation range of 0.1 to 100 ng/mL using 1 mL of blood. Collectively, the inter- and intra-day variabilities of sirolimus in quality control samples measured during validation were $\leq$12.7%, and biases were $\leq$11.3%.

For expression profiling analyses, total RNA was isolated from PBMC pellets using the RNeasy mini kit (Qiagen, Valencia, Calif.) and labeled probe for oligonucleotide arrays was prepared using a modification of the procedure described by Lockhart, et al., NAT. BIOTECHNOL., 14:1675-1680 (1996). Labeled probes were hybridized to oligonucleotide arrays comprised of over 12,600 human sequences (HgU95A, Affymetrix) according to the Affymetrix Expression Analysis Technical Manual (Affymetrix). Expression levels expressed as "average difference" and absent/present call determinations were computed from raw fluorescent intensity values using GENECHIP 3.2 software (Affymetrix, Santa Clara, Calif.). "Present" calls are calculated by GENECHIP 3.2 software by estimating whether a transcript is detected in a sample based on the strength of the gene's signal compared to background. The "average difference" values for each transcript were normalized to "frequency" values using the scaled frequency normalization method (Hill, et al, GENOME BIOL. 2:research0055.1-0055.13 (2001)) in which the average differences for 11 control cRNAs with known abundance spiked into each hybridization solution were used to generate a global calibration curve. This calibration was then used to convert average difference values for all transcripts to frequency estimates, stated in units of parts per million ranging from 1:300,000 (~3 parts per million (ppm)) to 1:1000 (1000 ppm).

Arrays may be hybridized for 16 hours at 45° C. The hybridization buffer includes 100 mM MES, 1 M [Na$^+$], 20 mM EDTA, and 0.01% Tween 20. After hybridization, the cartridges can be washed extensively with wash buffer (6×SSPET), for instance, three 10-minute washes at room temperature. These hybridization and washing conditions are collectively referred to as "nucleic acid array hybridization conditions." The washed cartridges can then be stained with phycoerythrin coupled to streptavidin. 12×MES stock contains 1.22 M MES and 0.89 M [Na$^+$]. For 1000 ml, the stock can be prepared by mixing 70.4 g MES free acid monohydrate, 193.3 g MES sodium salt and 800 ml of molecular biology grade water, and adjusting volume to 1000 ml. The pH can arrange between 6.5 and 6.7. 2× hybridization buffer can be prepared by mixing 8.3 ml of 12×MES stock, 17.7 mL of 5 M NaCl, 4.0 mL of 0.5 M EDTA, 0.1 mL of 10% Tween 20 and 19.9 mL of water. 6×SSPET contains 0.9 M NaCl, 60 mM NaH$_2$PO$_4$, 6 mM EDTA, pH 7.4, and 0.005% Triton X-100. In some cases, the wash buffer can be replaced with a more stringent wash buffer. 1000 ml stringent wash buffer can be prepared by mixing 83.3 mL of 12×MES stock, 5.2 mL of 5 M NaCl, 1.0 mL of 10% Tween 20 and 910.5 mL of water.

Example 3

Correlation of Pharmacokinetic Parameters to Gene Expression

PBMC gene expression data were normalized by the scaled frequency normalization method as described above. Expression profiling analysis of the 45 baseline PBMC samples, 33 week 8 samples, and 23 week 16 samples revealed that of the 12,626 genes on the HgU95A chip, 5,469 genes met the initial criteria for further analysis (at least 1 present call across the dataset, and at least 1 transcript with a frequency $\geq$10 ppm). The filter which removes transcripts called absent in all samples is based upon the absent/present decision call made by the GENECHIP 3.2 software, which reflects the relative intensity of hybridization of the labeled probes to perfectly matched oligonucleotides versus hybridization to mismatched oligonucleotides for each transcript on the HgU95A chip. The filter that removes transcripts with a frequency of less than 10 ppm in all samples is designed to remove low abundance transcripts which may have variable expression in technical replicates.

Following this data reduction step, a Spearman's rank correlation test was used to correlate the individually derived exposure metrics of cumulative CCI-779 AUC and cumulative AUC$_{sum}$ observed at 8 or 16 weeks with either (1) static expression levels of PBMC transcripts at 8 or 16 weeks, or (2) changes in expression from pretreatment levels to 8 or 16 weeks in patient PBMCs. Changes from pretreatment levels were calculated based on log-transformed expression levels. As used herein, AUC and AUC$_{sum}$ denote the Bayesian estimate of the area under the concentration-time curves for parent drug (e.g., CCI-779) and parent plus metabolite, respectively.

Example 4

Pharmacogenomic Analysis

Pairwise correlations were calculated to assess the association between individually derived exposure metrics and gene expression levels measured by HgU95A Affymetrix microarrays during the course of therapy. Correlations were run for two pharmacokinetic parameters—cumulative AUC and cumulative AUC$_{sum}$, and for four measures of expression level—log$_2$-transformed scaled frequency at 8 weeks, log$_2$-transformed scaled frequency at 16 weeks, the difference between log$_2$-transformed scaled frequency at 8 weeks and baseline, and the difference between log$_2$-transformed scaled frequency at 16 weeks and baseline.

Spearman's rank correlations, which are not sensitive to potential non-normal distributional properties of the pharmacokinetic parameters, were computed. The p-value for the hypothesis that the correlation was equal to 0 was calculated for each pairwise correlation. For each comparison between pharmacokinetic parameters and gene expression, the number of tests that were nominally significant out of the 5,469 tests performed was calculated for five Type I (i.e. false-positive) error levels.

The overall results for Spearman's rank correlation comparisons of pharmacokinetic parameters with expression levels are summarized in Table 4. Table 4 includes the results for comparisons of static PBMC transcript levels at 8 or 16 weeks, or changes in expression levels at 8 or 16 weeks from pre-treatment levels, with the pharmacokinetic parameters of cumulative AUC or cumulative $AUC_{sum}$. Statistical significance levels, the expected numbers of transcripts out of 5,469 that would have statistically significant tests at the given significance level, and the observed numbers of transcripts with statistically significant correlations are also presented.

To appropriately adjust for the fact that 5,469 non-independent tests were performed, a permutation-based approach was employed to evaluate how often the observed number of significant tests would be found under the null hypothesis of no correlation. The observed numbers of transcripts with changes from baseline that were correlated with the independently derived exposure metric of cumulative $AUC_{sum}$ are presented. The associated percentages of permutations (out of 1000 tests) resulting in nominally significant Spearman's correlations equal to or greater than the number observed for each given significance level are also presented.

The results of permutation tests run for cumulative $AUC_{sum}$ vs expression change at 8 weeks and at 16 weeks are shown in Tables 5a and 5b. The permutation results indicate that there was reasonably strong evidence for an association between cumulative $AUC_{sum}$ and the changes in gene expression in numerous transcripts at 8 or 16 weeks compared to pre-treatment levels. Table 6 presents the results of the correlations at 8 weeks and 16 weeks for each of the 19 transcripts whose frequency changes from baseline at 16 weeks were significantly correlated to $AUC_{sum}$ ($p \leq 0.01$). Table 6 also includes FARP1 (Accession No. A1701049). The change in expression level of FARP1 at 16 weeks relative to baseline level was also significantly correlated to $AUC_{sum}$. Accession numbers for the 19 transcripts are presented in Table 6, along with columns indicating the coefficient of variation observed in healthy individuals (% CV), the p-value observed in the Spearman correlation, the actual magnitude of the correlation, and the corresponding gene names.

TABLE 5a

Permutation Results for Spearman's Correlations of Changes in PBMC Gene Expression at 8 weeks with $AUC_{sum}$
$AUC_{sum}$ vs Log2 scaled frequency change from baseline at week 8

| Statistical significance level | Observed Number of Nominally Significant Spearman Correlations* | Percent of Permutations for which Number of Nominally Significant Spearman Correlations Equals or Exceeds Observed Number |
| --- | --- | --- |
| 0.1 | 584 | 34.0% |
| 0.05 | 286 | 34.5% |
| 0.01 | 60 | 29.6% |
| 0.005 | 30 | 29.4% |
| 0.001 | 8 | 22.0% |

TABLE 5b

Permutation Results for Spearman's Correlations of Changes in PBMC Gene Expression at 16 weeks with $AUS_{sum}$
$AUC_{sum}$ vs Log2 scaled frequency change from baseline at week 16

| Statistical significance level | Observed Number of Nominally Significant Spearman Correlations* | Percent of Permutations for Which Number of Nominally Significant Spearman Correlations Equals or Exceeds Observed Number |
| --- | --- | --- |
| 0.1 | 747 | 20.0% |
| 0.05 | 415 | 18.1% |
| 0.01 | 111 | 13.9% |
| 0.005 | 64 | 13.0% |
| 0.001 | 19 | 9.2% |

TABLE 4

Results for Spearman's Correlations of Gene Expression with Pharmacokinetic Parameters

| | | 8 weeks | | | | 16 weeks | | | |
| --- | --- | --- | --- | --- | --- | --- | --- | --- | --- |
| | | $AUC_{sum}$ vs | | CCI AUC vs | | $AUC_{sum}$ vs | | CCI AUC vs | |
| Statistical significance level | Expected no. of significant qualifiers | Expression level | Change from baseline level | Expression level | Change from baseline level | Expression level | Change from baseline level | Expression level | Change from baseline level |
| 0.05 | 273 | 197 | 286 | 284 | 173 | 289 | 415 | 359 | 281 |
| 0.01 | 55 | 27 | 60 | 43 | 28 | 42 | 111 | 63 | 51 |
| 0.001 | 5 | 0 | 8 | 1 | 1 | 5 | 19 | 4 | 7 |

TABLE 6

Transcripts with Changes in Expression Level at 16 Weeks Significantly Correlated to $AUC_{sum}$

| Accession No. | Gene Name | Average % CV in healthy individuals | Correlation with $AUC_{sum}$ at 8 weeks | P-value (8 weeks) | Correlation with $AUC_{sum}$ at 16 weeks | P-value (16 weeks) |
|---|---|---|---|---|---|---|
| U44839 | USP11 | 18 | 0.16 | 0.3998 | 0.76 | 0.0001 |
| AI762438 | U2AF65 | 21 | 0.23 | 0.2209 | 0.74 | 0.0001 |
| U90917 | FOXM1 | 30 | 0.24 | 0.206 | 0.75 | 0.0001 |
| AF038661 | B4GALT3 | 15 | 0.21 | 0.2589 | 0.73 | 0.0002 |
| AL046394 | UNK_AL046394 | 20 | 0.31 | 0.0999 | 0.72 | 0.0002 |
| AI540925 | COX6A1 | 10 | −0.50 | 0.0050 | −0.73 | 0.0002 |
| H98552 | UNK_H98552 | 30 | 0.39 | 0.0308 | 0.71 | 0.0003 |
| U48734 | ACTN4 | 22 | 0.33 | 0.0721 | 0.71 | 0.0003 |
| AI147237 | UNK_AI147237 | 27 | 0.32 | 0.0877 | 0.70 | 0.0004 |
| M19309 | TNNT1 | 80 | 0.21 | 0.2684 | 0.70 | 0.0004 |
| J05257 | DPEP1 | 39 | 0.39 | 0.0348 | 0.69 | 0.0005 |
| AL022318 | UNK_AL022318 | 22 | 0.21 | 0.2617 | 0.69 | 0.0005 |
| U92315 | SULT2B1 | 34 | 0.30 | 0.1066 | 0.69 | 0.0005 |
| AF070548 | SLC25A11 | 29 | 0.32 | 0.0881 | 0.69 | 0.0006 |
| AB020664 | KIAA0857 | 45 | 0.01 | 0.9627 | 0.69 | 0.0006 |
| M14565 | CYP11A | 22 | 0.32 | 0.0838 | 0.69 | 0.0006 |
| U17566 | SLC19A1 | 28 | 0.29 | 0.1220 | 0.68 | 0.0007 |
| AF074382 | IKBKG | 28 | 0.30 | 0.1013 | 0.68 | 0.0007 |
| M79463 | PML | 22 | 0.38 | 0.0378 | 0.68 | 0.0007 |
| AI701049 | FARP1 | | 0.47 | 0.0089 | 0.66 | 0.001 |

Example 5

Population Pharmacokinetic Analyses

In order to characterize the pharmacokinetic profiles of patients providing sparse blood sampling, fully and sparsely sampled patient data were analyzed collectively using a population pharmacokinetic method and the NONMEM application (version 1.0, Revision 5.0 on Windows NT 4.0 computer with Pentium processor, NONMEM Project Group, University of California at San Francisco, Calif.). Preliminary efforts to analyze parent and metabolite with a common model were unsuccessful and thought attributable to complexities of competition for specific binding in red blood cells, to the high multi compartmental nature of disposition, and to uncertainty in fraction of drug metabolized. Data were therefore modeled separately and segregated by analyte into two separate data sets with dose, time/duration of administration, and demographic information. In addition, a determinant factor of survival for renal cancer patients as described by Motzer, et al., J. CLIN. ONCOL., 17:2530-2540 (1999) was also included as a covariate. Construction of the NONMEM infile was performed using SAS (version 8.1) on a Sun Microsystems mainframe computer with Sun OS 5.8. For CCI-779, a three-compartment model with zero-order infusion was found to most adequately describe the data. For sirolimus, a two-compartment model with $1^{st}$ order input was appropriate. In both cases, the model-derived value for AUC for a given patient and analyte were obtained from the quotient of CCI-779 Dose/Clearance (CL), in which CL was obtained from Bayesian estimation and the POSTHOC option of NONMEM.

During model building, an exponential error model was applied to the kinetic model. A proportional model best described the intra-individual residual error. To assess goodness of fit, the criteria described by Pai, et al., J. CLIN. PHARMACOL., 32:242-247 (1992) were considered and include: (1) decrease of the objective function (OF) of more than 3.84 (p<0.05) during model building, and more than 7.88 (p<0.005) during model reduction (p-values assume a chi-square distribution); (2) minimization of the standard errors with respect to the parameter estimates; (3) random scatter of points around the line of identity in plots of weighted residual-versus-predicted concentrations; (4) minimization of inter-individual variances and an improvement in their precision; and (5) a reduction in the magnitude of residual variability.

Example 6

Results of Population Pharmacokinetic Analyses

Mean demographic factors of patients providing samples for population analysis are shown in Table 7. The typical demographic profile of patients was that of a 58 year old, white (90%), male (66%), weighing 83 kg, and with a hematocrit of 38.1%.

TABLE 7

Demography Summary of Patients Included in Population Pharmacokinetic Analysis of CCI-779 and Sirolimus

| Characteristic | Total (n = 50) |
|---|---|
| Age, year | |
| Mean ± Standard Deviation | 57.8 ± 9.6 |
| Median | 57.5 |
| Minimum-Maximum | 40-81 |
| Sex, n (%) | |
| Female | 17 (34) |
| Male | 33 (66) |
| Ethnic Origin, n (%) | |
| Black | 2 (4) |
| Hispanic | 3 (6) |
| Caucasian | 45 (90) |

TABLE 7-continued

Demography Summary of Patients Included in Population Pharmacokinetic Analysis of CCI-779 and Sirolimus

| Characteristic | Total (n = 50) |
|---|---|
| Weight, kg | |
| Mean ± Standard Deviation | 83.1 ± 15.8 |
| Median | 84.5 |
| Minimum-Maximum | 53.7-124.7 |
| Body Surface Area, m$^2$ | |
| Mean ± Standard Deviation | 1.97 ± 0.20 |
| Median | 1.99 |
| Minimum-Maximum | 1.62-54.5 |
| Hematocrit | |
| Mean ± Standard Deviation | 38.1 ± 5.8 |
| Median | 36.8 |
| Minimum-Maximum | 26.9-54.5 |
| Albumin, g/dL | |
| Mean ± Standard Deviation | 3.9 ± 0.5 |
| Median | 4.0 |
| Minimum-Maximum | 2.4-4.6 |

Blood samples from 90 patients were obtained from both fully and sparsely sampled patients for consideration in the population analyses. Of this number, 235 observations from 50 patients were ultimately included in the final analyses.

For CCI-779, a 3-compartment model was used with factors for non-linear dose effect, multiple dose decrease in exposure, and inter-patient variability. Observed steady-state concentrations of CCI-779 appear lower than expected from a linear prediction of accumulation. This phenomenon is empirically modeled in the present study with the DNUM variable for CCI-779 clearance (see Table 8). Covariate analysis revealed that body surface area (BSA) is a significant factor affecting CCI-779 clearance. Differences in age, gender, race or renal risk survival factor did not influence parent drug disposition. In Table 8, typical value (TV) for clearance term CL, Q2 and Q3 are defined as: $TVCL=1.39*(1+DNUM*0.103)*DOSE^{0.551}*BSA^{1.28}$. TV for clearance term Q2 defined as: $TVQ2=6.48*DOSE^{0.551}$. TV for clearance term Q3 defined as: $TVQ3=0.258*DOSE^{0.551}$. DNUM denotes effect following a single (DNUM=0) or multiple doses (DNUM=1).

The final model typical values were used to generate the profiles shown in FIGS. 1A, 1C, and 1E. In addition, the final model was internally validated using the bootstrap approach. Results of this analysis indicate that most of the final model estimates lie within the 5$^{th}$ and 95$^{th}$ percentile confidence limits of the bootstrap values (see Table 9 which was derived from 1,000 bootstrap sample runs). Exception to conformity was observed for inter-subject variability on V2, V3 and residual error. Bias between the final model and median bootstrap sample data appear low (<7%) for all the structural pharmacokinetic parameters between the final and median bootstrap values. Somewhat higher differences for the pharmaco-statistical parameters for intersubject and residual variabilities were seen. This is thought to occur when a dataset is limited in size for a given model, or the model exhibits a substantial degree of parameterization relative to the dataset.

For sirolimus, a 2-compartment model with apparent first-order formation into the central compartment was used. In this model, factors for non-linear dose effect on apparent clearance and inter-patient variability are incorporated. An analysis to identify demographic factors of variability indicated that hematocrit is a significant covariate of sirolimus volume of distribution. Final results are shown in Table 10 and FIGS. 1B, 1D, and 1F. In Table 10, TV for clearance term CL is defined as: $TVCL=2.05*DOSE^{0.422}$. TV for volume term V3 defined as: $TVV3=12.9*DOSE^{0.302}*HCT^{0.719}$.

The final model for sirolimus was also validated through bootstrap. Results of this analysis are shown in Table 11 and indicate that most of the final model estimates lie within the 5$^{th}$ and 95$^{th}$ percentile of confidence limits of the bootstrap values (derived from 1,000 bootstrap sample runs). In addition, bias between the final model and median bootstrap sample data appears moderate (<38%) for all the structural pharmacokinetic parameters between the final and median bootstrap values. Higher differences for the structural and pharmaco-statistical parameters for intersubject and residual pharmaco-statistical parameters for intersubject and residual variabilities were observed and thought due both to limitations in the dataset for the given model, and also from its nature as metabolite data which is typically inherently more variable.

TABLE 8

Final Model Typical Values of Pharmacokinetic Parameters for CCI-779

| | $\theta_1$ CL (L/h) | $\theta_2$ V1 (L) | $\theta_3$ Q2 (L/h) | $\theta_4$ V2 (L) | $\theta_5$ Q3 (L/h) | $\theta_6$ V3 (L) | $\theta_7$ DE | $\theta_8$ INTR | $\theta_8$ BSA effect |
|---|---|---|---|---|---|---|---|---|---|
| Parameter Estimate | 1.39 | 37.6 | 6.48 | 271 | 0.258 | 323 | 0.551 | 0.103 | 1.28 |
| Precision of Estimate % | 29.9 | 14.8 | 14.4 | 11.5 | 24.0 | 18.5 | 6.5 | 35.0 | 0.455 |
| Inter-Patient Variability % | 23.7 | — | — | 44.1 | — | 129 | | | |

TABLE 9

Results Validation of Final Population Pharmacokinetic Model for CCI-779

| Parameter | Units | Symbol | Bootstrap Sample 5th Percentile | Bootstrap Sample 95th Percentile | Median | Final Model Parameter Estimate | % Difference |
|---|---|---|---|---|---|---|---|
| CL | L/h | $\theta_1$ | 0.76 | 2.56 | 1.45 | 1.39 | 4.3 |
| V1 | L | $\theta_2$ | 27.7 | 47.2 | 38.3 | 37.6 | 1.9 |
| Q2 | L/h | $\theta_3$ | 4.77 | 9.13 | 6.46 | 6.48 | −0.3 |
| V2 | L | $\theta_4$ | 224 | 337 | 275 | 271 | 1.5 |
| Q3 | L/h | $\theta_5$ | 0.164 | 0.430 | 0.267 | 0.258 | 3.5 |
| V3 | L | $\theta_6$ | 139 | 1311 | 339 | 323 | 5.0 |
| Dose effect on CL | — | $\theta_7$ | 0.480 | 0.629 | 0.553 | 0.551 | 0.4 |
| Inter-period variability on CL | — | $\theta_8$ | 0.049 | 0.218 | 0.110 | 0.103 | 6.8 |
| BSA on CL | — | $\theta_9$ | 0.405 | 2.07 | 1.21 | 1.28 | −5.5 |
| Intersubject variability on CL | — | $\omega^2_1$ | 0.028 | 0.412 | 0.215 | 0.056 | 283.9 |
| Intersubject variability on V2 | — | $\omega^2_2$ | 0.222 | 0.641 | 0.414 | 0.194 | 113.4 |
| Intersubject variability on V3 | — | $\omega^2_3$ | 0.247 | 1.56 | 1.08 | 1.67 | −35.3 |
| Proportional error | — | $\epsilon^2$ | 0.335 | 0.436 | 0.383 | 0.157 | 143.9 |

TABLE 10

Final Model Typical Values of Pharmacokinetic Parameters for Sirolimus

| | $\theta_1$ CL (L/h) | $\theta_2$ V2 (L) | $\theta_3$ Q (L/h) | $\theta_4$ V3 (L) | $\theta_5$ Ka (h$^{-1}$) | $\theta_6$ DE on CL | $\theta_7$ DE on V3 | $\theta_8$ HCT effect on V3 |
|---|---|---|---|---|---|---|---|---|
| Parameter Estimate | 2.05 | 10.4 | 44.1 | 12.9 | 0.087 | 0.422 | 0.302 | 0.719 |
| Precision of Estimate % | 29.5 | 42.5 | 60.3 | 26.9 | 50.2 | 14.5 | 27.2 | 13.9 |
| Inter-Patient Variability % | 63.7 | 164 | — | 22.8 | 34.6 | — | — | — |

TABLE 11

Results Validation of Final Population Pharmacokinetic Model for Sirolimus

| Parameter | Units | Symbol | Bootstrap Sample 5th Percentile | Bootstrap Sample 95th Percentile | Median | Final Model Parameter Estimate | % Difference |
|---|---|---|---|---|---|---|---|
| CL | L/h | $\theta_1$ | 1.05 | 3.13 | 1.99 | 2.05 | −2.9 |
| V2 | L | $\theta_2$ | 2.06 | 15.6 | 8.24 | 10.4 | −20.8 |
| Q | L/h | $\theta_3$ | 4.88 | 60.7 | 27.5 | 44.1 | −37.6 |
| V3 | L | $\theta_4$ | 1.28 | 81.6 | 11.6 | 12.9 | −10.1 |
| $k_a$ | h$^{-1}$ | $\theta_5$ | 0.0218 | 0.118 | 0.0616 | 0.087 | −29.2 |
| Dose effect on CL | — | $\theta_7$ | 0.305 | 0.545 | 0.412 | 0.422 | −2.4 |
| Dose effect on V3 | — | $\theta_8$ | 0.055 | 0.414 | 0.231 | 0.302 | −23.5 |
| Hematocrit effect on V3 | — | $\theta_9$ | 0.314 | 1.41 | 0.768 | 0.719 | 6.8 |
| Intersubject variability on CL | — | $\omega^2_1$ | 0.382 | 0.930 | 0.545 | 0.406 | 34.2 |
| Intersubject variability on V2 | — | $\omega^2_2$ | 0.592 | 4.843 | 1.418 | 2.72 | −47.9 |
| Intersubject variability on V3 | — | $\omega^2_3$ | 0.000 | 0.363 | 0.179 | 0.052 | 244.2 |
| Intersubject variability on $k_a$ | — | $\omega^2_4$ | 0.175 | 0.424 | 0.316 | 0.120 | 163.3 |
| Proportional error | — | $\epsilon^2$ | 0.166 | 0.278 | 0.212 | 0.0543 | 290.4 |

Example 7

Pharmacodynamic Analyses—Safety

Correlation of drug exposure (AUC$_{sum}$ and CCI-779 AUC) to safety endpoints were performed to evaluate if the severity of a given adverse event (AE) was significantly associated with single dose or cumulative dose drug exposure. For the cumulative dose drug exposure, cumulative AUC$_{sum}$ was determined. Each patients' specific dosing history while on trial medication was determined and used to derive respective AUCs experienced by each patient for the duration of time from start of treatment to time of highest severity adverse event. This test included all the data, irrespective of AE severity, and was analyzed using the asymptotic Mantel-Haenszel Test for Ordinal Association. A severity score of "1" indicating the lowest severity and "3" indicating the highest severity was used. A "0" score indicated that the AE was not experienced by the patient. Pharmacokinetic parameters were grouped into low, medium and high categories with an equal number of patients in each category. Given the general utilitarian value of this method as an exploratory screening technique, a p-value <0.05, without adjustment for multiple comparisons, was considered indicative of a potentially clinically relevant association.

Correlations of drug exposure ($AUC_{sum}$ and cumulative $AUC_{sum}$) to safety endpoints were also performed to evaluate if the duration of a given adverse event was significantly associated with single dose or cumulative dose drug exposure. Estimation of cumulative exposure was determined for each patient as described above. Duration of an AE was determined by calculating the time interval for which a given patient experienced a given AE. Only patients who exhibited an AE were included in this test. The correlations between AE duration and the continuous pharmacokinetic variables were calculated using Spearman rank correlation test (SAS Institute Inc., SAS® LANGUAGE REFERENCE, Version 8, Cary, N C: SAS Institute Inc., 1999). A p-value <0.05 was considered indicative of a potentially clinically relevant association.

Example 8

Results of Pharmacodynamic Analyses

Results of the pharmacodynamic analysis using $AUC_{sum}$ (discrete predictor), cumulative $AUC_{sum}$ (cumulative predictor variable), $C_{eoi}$ (peak exposure predictor) are shown in Table 12 as derived from 49 differing adverse events recorded for those patients included in the population analysis. $AUC_{sum}$ refers to algebraic sum of CCI-779 and sirolimus area under the curve. Cumulative $AUC_{sum}$ refers to aggregate $AUC_{sum}$ based on individual patient dosing history. $C_{eoi}$ is the CCI-779 concentration observed at end of infusion. AEs with correlation p-values of less than 0.05 are listed in bold.

ciated with increased duration of thrombocytopenia (p=0.015), and dry mouth (p=0.036).

The effect of cumulative exposures indicate interesting associations between cumulative $AUC_{sum}$ and AE severity are present for acne (p=0.003), infection (p=0.003), mucositis (p=0.004), nail discoloration (p=0.005), pruritis (p=0.011), and macropapular rash (p=0.012), and cough (0.05). Similarly, correlations between cumulative $AUC_{sum}$ and AE duration indicate that increased exposure is associated with increased duration of rash (p<0.001), anorexia (p=0.001), hyperglycemia (p=0.019), diarrhea (p=0.03), and macropapular rash (p=0.046). A negative correlation was also observed with headache (p=0.03). Interestingly, thrombocytopenia, which was a significant and frequent AE, appeared to be not significant for the cumulative metric, probably because thrombocytopenia was a frequent cause for consideration to reduce or withhold dose.

For end of infusion concentrations, associations with AE severity are observed for myalgia (p=0.013), and fever (p=0.022). Similarly, correlations between $C_{eoi}$ and AE duration were also examined and indicate significant associations with abdominal pain (p=0.01), and anorexia (p=0.015). In addition, a negative correlation was also observed with fever (p=0.04).

In the above examples, the pharmacokinetic profile of CCI-779 was characterized using a mixed sampling design in

TABLE 12

Pharmacodynamic Correlation of Various Exposure Prediction Metrics and Duration of Adverse Event

| | N patients | P-value (Spearman correlation to $AUC_{sum}$) | P-value (Spearman correlation to cumulative $AUC_{sum}$) | P-value (Spearman correlation to Ceoi) |
|---|---|---|---|---|
| CORRELATION TO SEVERITY | | | | |
| Thrombocytopenia | 15 | 0.007 (0.3374) | 0.834 | 0.414 |
| Pruritis | 22 | 0.011 (0.3896) | 0.011 (0.3696) | 0.342 |
| Hyperlipemia | 15 | 0.040 (0.2625) | 0.088 | 0.187 |
| Acne | 19 | 0.214 | 0.003 (0.4607) | 0.069 |
| Infection | 22 | 0.846 | 0.003 (0.4227) | 0.162 |
| Mucositis | 18 | 0.655 | 0.004 (0.3813) | 0.194 |
| Nail Discoloration | 10 | 0.351 | 0.005 (0.4807) | 0.656 |
| Rash Mac Pap | 16 | 0.530 | 0.012 (0.4130) | 0.816 |
| Cough Inc | 21 | 0.663 | 0.050 (0.3365) | 0.610 |
| Myalgia | 13 | 0.519 | 0.197 | 0.013 (0.414) |
| Fever | 17 | 0.317 | 0.803 | 0.022 (0.402) |
| CORRELATION TO DURATION | | | | |
| Thrombocytopenia | 15 | 0.015 (0.616) | 0.374 | 0.509 |
| Dry mouth | 6 | 0.036 (0.841) | 0.538 | 0.368 |
| Rash | 40 | 0.240 | <0.001 (0.515) | 0.308 |
| Anorexia | 22 | 0.428 | 0.001 (0.667) | 0.015 (0.597) |
| Hyperglycemia | 14 | 0.802 | 0.019 (0.636) | 0.803 |
| Diarrhea | 22 | 0.422 | 0.030 (0.474) | 0.111 |
| Headache | 10 | 0.551 | 0.030 (−0.681) | 0.175 |
| Rash Mac Pap | 16 | 0.629 | 0.046 (0.522) | 0.427 |
| Pain abdomen | 13 | 0.699 | 0.434 | 0.01 (0.873) |
| Fever | 17 | 0.481 | 0.844 | 0.04 (−0.626) |

Clinically interesting associations between $AUC_{sum}$ and AE severity are observed for thrombocytopenia (p=0.007), pruritus (p=0.011), and hyperlipemia (p=0.040). Similarly, correlations between $AUC_{sum}$ and AE duration were also examined and indicate that increased $AUC_{sum}$ values are associated which one subset of patients was extensively sampled during cycles 1 and 4, and the remainder of patients was sparsely sampled during cycle 4 only.

One hallmark of CCI-779 pharmacokinetics is the drug's specific binding to FKBP; an attribute thought to augment the poly-exponential character of disposition when measured from whole blood. To describe CCI-779 pharmacokinetics, a three-compartment model with zero-order infusion was used. Parent and metabolite kinetics could not be optimally characterized with a common model therefore sirolimus disposition was described using a separate two-compartment model with $1^{st}$ order input. In addition, functions that account for less-than proportional exposure with dose and with repeated dosing (CCI-779 only) were found to significantly minimize variability of the model and were included. The final model for CCI-779 also incorporated a covariate for BSA on clearance. For a given dose, clearance of CCI-779 increases approximately 45% when administered to patients with BSA values that range from 1.5 to 2 $m^2$. While substantial, previous data had shown that the effect of BSA on total (CCI-779 plus sirolimus) concentrations in blood is negligible, and was confirmed in the present study by simulation. As expected with a drug that specifically binds to red blood cells, the hematocrit exerted an important effect on sirolimus concentrations, with decreasing hematocrit causing an overall decrease in composite drug concentrations.

To evaluate possible exposure-response relationships to safety, discrete ($C_{eoi}$, $AUC_{sum}$) and composite (cumulative $AUC_{sum}$) Bayesian predictor variables were collated or derived for individual patients. The intent of the pharmacodynamic analysis was to screen for potential relationships between drug exposure and AE severity/duration as an aid to identification of treatment-emergent effects. Analysis involved statistical testing without correction for multiple comparisons. While it is recognized that lack of correction could increase the potential for type II error, this was considered acceptable for the aim of an exploratory analysis. It is envisioned that application of this approach may provide insights into the temporal relationship of CCI-779 treatment with safety and tolerability.

The search for transcriptional biomarkers correlated with drug exposure in surrogate tissues (e.g., PBMCs) represents an important application of clinical pharmacogenomics in the field of oncology. Previously, clinical pharmacogenomics has focused on studies examining the expression profiles of primary tumors. The accessibility of surrogate tissues and the ability to perform rapid and non-invasive sampling for the analysis of drug effects will undoubtedly drive the search for expression profiles in these tissues in clinical trials in the future.

One of the pharmacogenomic objectives in the above examples was the identification of transcripts in PBMCs that appeared to covary with independently-derived exposure metrics for patients in the study. By correlating exposure to expression, this analysis identified 19 transcripts with alterations in expression from pretreatment levels that were significantly correlated (e.g., $p \leq 0.01$, 0.005, 0.001, or less) with individual values for cumulative $AUC_{sum}$ measured in the patients receiving CCI-779. The directions of the correlations (positive or negative) of the individual transcripts with CCI-779 exposure were conserved at 8 and 16 weeks for every transcript in Table 6.

In addition, we analyzed expression profiles from PBMCs harvested at 8 week intervals (n=3 time points) from 10 disease-free individuals in order to determine transcripts in peripheral blood that appear to vary naturally over a similar time course as measured in the present study. A coefficient of variation was calculated using a one-way ANOVA to estimate within individual variation for each transcript. Only one of the transcripts in Table 6, troponin (TNNT1), was found to possess a high (>80%) average coefficient of variation in PBMCs from normal individuals measured over time. The remaining transcripts did not vary significantly (average CVs ranging between 10 and 45%) in disease-free individuals' PBMCs measured at different time points, suggesting that the variation in the remaining transcripts in CCI-779 treated RCC patients can be explained by the presence of drug.

A phase 3 clinical trial of CCI-779 in renal cell carcinoma will compare clinical outcomes for patients receiving IFN-alpha alone (standard of care), CCI-779 plus IFN-alpha, or CCI-779 alone. This upcoming study will enable comparison of longitudinal expression profiles in the 3 different therapy groups and afford an opportunity to verify the transcriptional changes observed in the present study that appear to be specific to CCI-779 exposure in vivo.

The foregoing description of the present invention provides illustration and description, but is not intended to be exhaustive or to limit the invention to the precise one disclosed. Modifications and variations are possible consistent with the above teachings or may be acquired from practice of the invention. Thus, it is noted that the scope of the invention is defined by the claims and their equivalents.

What is claimed is:

1. A method for monitoring CCI-779 activity in a patient having a non-blood disease, the method comprising:
   (a) generating an expression profile of an ubiquitin specific protease 11 (USP11) gene in a peripheral blood sample obtained from the patient having the non-blood disease and at a stage of treatment with CCI-779, wherein the expression profile is generated by isolating a plurality of ribonucleic acid (RNA) molecules from the peripheral blood sample, labeling said plurality of RNA molecules with a labeling moiety, and probing said plurality of RNA molecules for the presence of a USP11 RNA;
   (b) comparing the expression profile of said USP11 gene generated from step (a) to a reference expression profile of said USP11 gene; and
   (c) making a determination of CCI-779 activity in the patient based on the comparison result from step (b), wherein
      (i) the determination is provided to a user,
      (ii) said USP11 gene is differentially expressed in peripheral blood mononuclear cells (PBMCs) of patients who have the non-blood disease during the treatment with CCI-779 as compared to PBMCs of said patients before the treatment, and
      (iii) the non-blood disease is a solid tumor.

2. A method for monitoring CCI-779 activity in a patient having a non-blood disease, the method comprising:
   (a) generating an expression profile of at least one CCI-779 activity gene in a peripheral blood sample obtained from the patient having the non-blood disease and at a stage of treatment with CCI-779, wherein the expression profile is generated by isolating a plurality of ribonucleic acid (RNA) molecules from the peripheral blood sample, labeling said plurality of RNA molecules with a labeling moiety, and probing said plurality of RNA molecules for the presence of one or more CCI-779 activity RNAs set forth in Table 1;
   (b) comparing the expression profile of said at least one CCI-779 activity gene generated from step (a) to a reference expression profile of said at least one CCI-779 activity gene; and
   (c) making a determination of CCI-779 activity in the patient based on the comparison result from step (b), wherein,
      (i) the determination is provided to a user,
      (ii) said at least one CCI-779 activity gene is a gene that is differentially expressed in peripheral blood mononuclear cells (PBMCs) of patients who have the non-blood disease during the treatment with CCI-779 as compared to PBMCs of said patients before the treatment,
      (iii) the non-blood disease is a solid tumor,
      (iv) the expression profile of said at least one CCI-779 activity gene comprises an expression level of said at least one CCI-779 activity gene,
      (v) the expression level is an absolute level, a normalized level, or a relative level of said at least one CCI-779 activity gene,
      (vi) the determination of the CCI-779 activity is based on an increase or decrease of the expression level of said at least one CCI-779 activity gene by at least 2-fold compared to the reference expression level, and
      (vii) the at least one CCI-779 activity gene is selected from the group of genes set forth in Table 1.

3. A method for monitoring CCI-779 activity in a patient having a non-blood disease, the method comprising:
   (a) generating an expression profile of an ubiquitin specific protease 11 (USP11) gene in a peripheral blood sample obtained from the patient having the non-blood disease and at a stage of treatment with CCI-779, wherein the expression profile is generated by isolating ribonucleic acid (RNA) molecules from the peripheral blood sample, and hybridizing said RNA molecules to a plurality of nucleic acid probes, wherein the plurality of nucleic acid probes comprises a ubiquitin protease 11 (USP11) nucleic acid probe;
   (b) comparing the expression profile of said USP11 gene generated from step (a) to a reference expression profile of said USP11 gene; and
   (c) making a determination of CCI-779 activity in the patient based on the comparison result from step (b), wherein (i) the determination is provided to a user, (ii) said USP11 gene is differentially expressed in peripheral blood mononuclear cells (PBMCs) of patients who have the non-blood disease during the treatment with CCI-779 as compared to PBMCs of said patients before the treatment, and (iii) the non-blood disease is a solid tumor.

4. A method for monitoring CCI-779 activity in a patient having a non-blood disease, the method comprising:
   (a) generating an expression profile of at least one CCI-779 activity gene in a peripheral blood sample obtained from the patient having the non-blood disease and at a stage of treatment with CCI-779, wherein the expression profile is generated by isolating ribonucleic acid (RNA) molecules from the peripheral blood sample, and hybridizing said RNA molecules to a plurality of nucleic acid probes, wherein the plurality of nucleic acid probes comprises one or more CCI-779 activity gene probes;
   (b) comparing the expression profile of said at least one CCI-779 activity gene generated from step (a) to a reference expression profile of said at least one CCI-779 activity gene; and
   (c) making a determination of CCI-779 activity in the patient based on the comparison result from step (b), wherein, (i) the determination is provided to a user, (ii) said at least one CCI-779 activity gene is a gene that is differentially expressed in peripheral blood mononuclear cells (PBMCs) of patients who have the non-blood disease during the treatment with CCI-779 as compared to PBMCs of said patients before the treatment, (iii) the non-blood disease is a solid tumor, (iv) the expression profile of said at least one CCI-779 activity gene comprises an expression level of said at least one CCI-779 activity gene, (v) the expression level is an absolute level, a normalized level, or a relative level of said at least one CCI-779 activity gene, (vi) the determination of the CCI-779 activity is based on an increase or decrease of the expression level of said at least one CCI-779 activity gene by at least 2-fold compared to the reference expression level, and (vii) the at least one CCI-779 activity gene is selected from the group of genes set forth in Table 1.

* * * * *

SEQUENCE LISTING

```
<160> NUMBER OF SEQ ID NOS: 20

<210> SEQ ID NO 1
<211> LENGTH: 559
<212> TYPE: DNA
<213> ORGANISM: Homo sapiens

<400> SEQUENCE: 1
cggccagtgg cactactttg atgacaacag cgtctcccct gtcaatgaga atcagatcga        60
gtccaaggca gcctatgtcc tcttctacca acgccaggac gtggcgcgac gcctgctgtc       120
cccggccggc tcatctggcg ccccagcctc ccctgcctgc agctccccac ccagctctga       180
gttcatggat gttaattgag agccctgggt cctgccacag aaaaaaaaaa aaaaaagccc       240
tctctgcaat ctcgcttctc gtgtccgccc cgcttctctt attcgtgtta ggtgcccccg       300
ccaggcattg caggcttagt cgtggctact gttctcctgt gccgctgcat cgctctctcc       360
```

-continued

```
cgggaaagaa caggtcgtgt ctcctcctag cagtgcgcgc cccgcctgtg tttgcccttc    420
cagcagtgac cctcccttct agtctttatt tatggtcgtg cccttccctc tcctcagccc    480
agagtgttct gcgtgggtgg tgatgggggt tcacctgaac acagagtgta ttttcttatt    540
gaggccctgt accttctgc                                                 559
```

<210> SEQ ID NO 2
<211> LENGTH: 454
<212> TYPE: DNA
<213> ORGANISM: Homo sapiens
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (185)..(203)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t
<220> FEATURE:
<221> NAME/KEY: misc_feature
<222> LOCATION: (359)..(359)
<223> OTHER INFORMATION: n is a, c, g, or t
<220> FEATURE:
<221> NAME/KEY: misc_feature
<222> LOCATION: (414)..(415)
<223> OTHER INFORMATION: n is a, c, g, or t

<400> SEQUENCE: 2

```
atcatggcct cctcagtgat gccaaagggg atgttgccca cgtagaggcg ccgggcttgt     60
ctggtcatct ggctcccgac cacgggcacc ggcgntggng ncacagccag accgtcangg    120
gtcatggtgg gnagaaganc antggctgga atctgacccg cagcttgcat ggccttgtac    180
tgcannnnnn nnnnnnnnnn nnngcctggg ggtggcacgt cccagtattt acggaccttc    240
ttcttcttct cgtggcgggg ggaacgaatc agtccaccgt gctcctcttt agcgcctctg    300
gtcaaaggtt tgctgcgtcg tcgcctgtcc cgggangngc tccgctggtc ccggttgcnc    360
cggtcgcggc tccggctccg gcgtttgcgg tcccggctcc gagagcggct gtgnntgcgc    420
```
ttccgatgcc ggttctcctt gtcccgctct tgtt        454

<210> SEQ ID NO 3
<211> LENGTH: 432
<212> TYPE: DNA
<213> ORGANISM: Homo sapiens
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (132)..(133)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (206)..(266)
<223> OTHER INFORMATION: n is a, c, g, or t
<220> FEATURE:
<221> NAME/KEY: misc_feature
<222> LOCATION: (354)..(370)
<223> OTHER INFORMATION: n is a, c, g, or t

<400> SEQUENCE: 3
tcttcttgca ggaaagctga cttggaaaca cggggaggtg gcaggnaggg ncaaaangga        60
ctctggcaag cagatccact tgtntgggtc cctgcagtga agaacccaag atccaggtac        120
ctcagcctgg annaaaccgt gcactgcngg tcttcccttc tatcaaaact aaaagcangg        180
aacagaagtc aattgaaacc ncnggnnnnn nnnnnnnnnn nnnnnnnnnn        240
nnnnnnnnnn nnnnnnnnnn nnnnnntaat tagaggataa tttggagaat ttatactatt        300
tacacggacc accctgcaaa gatcagggaa ggctggattt cttcctcctt gatnnnnnnn        360
nnnnnnnnnn aaggagaaaa cccttctcca aacaggagtt tctcctctttt ccctggtcct        420 gcagaagaaa ga        432

<210> SEQ ID NO 4
<211> LENGTH: 568
<212> TYPE: DNA
<213> ORGANISM: Homo sapiens
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (197)..(199)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t

<400> SEQUENCE: 4

```
ggcctgggcc tctatctact gccaaccaca cagccctccg aggttcacac tgactcctcc    60
ttcctgtcta ccttaatcat gaaaccgaat tcatgggggtt gtattctccc caccctcagc   120
tcctcactgt tctcagaggg atgtgaggga actgaactct ggtgnccgtg ctaggggggtn   180
aggggnccte tccctcnnna ctgnctggna ctggnagctg ggctcctgta ganccctgnag  240
gggtccctct ctctagggtc tcctgtaggg cttatgactg tgaatccttg atgtcatgat   300
tttatgtgac gattcctagg agtccctgcc cctagagtag gagcagggct ggaccccaag   360
cccctccctc ttccatggag agaagagtga tctggcttct cctcggacct ctgtgaatat   420
ttattctatt tatggttccc gggaagttgt ttggtgaagg aagcccctcc ctgggcattt   480
tctgcctatg ctggaatagc tccctcttct ggtcctggct caggggggctg ggattttgat   540
atattttcta ataaaggact ttgtctcg                                     568
```

<210> SEQ ID NO 5
<211> LENGTH: 350
<212> TYPE: DNA
<213> ORGANISM: Homo sapiens

<400> SEQUENCE: 5

```
gtccagaact gttgcctgag acccctcctc tctcacacag ccctgccatg ctgactcggt    60
ttcccctcag agccattgtt gtctgggctc gagtttctgc cccaggttgt gtgctggaat   120
cggggggtgg ctctcctgcc acccatgggg agcgccagga gaggagggtc atggaggatg   180
ttggggctct gaccccagga gtggggtgga gggcggagcc tgctgggggc cctgccttca   240
cagagatgcc gcgtgctggg aaggctcttg gggtcccctg agcgtcttcc agggtggctg   300
gagagcacag acgcgccagg gagccccctc tgtgctcctc agagttcaat                350
```

<210> SEQ ID NO 6
<211> LENGTH: 218
<212> TYPE: DNA

```
<213> ORGANISM: Homo sapiens
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (181)..(182)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t

<400> SEQUENCE: 6
agatggtaac catactctat tccataaccc tcatgtgaat ccacnttcca actnggctac     60
gaagatgaat aaagagaatc tnggaccact acccngggca ccangggacc acnagcactg    120
gtttnggacc gttactctgc acantnggac cagaaaaagt atatnggggac cttaagctca   180 nnccttnctt tacttgtatc aaatgatgac tggtatac                            218

<210> SEQ ID NO 7
<211> LENGTH: 329
<212> TYPE: DNA
<213> ORGANISM: Homo sapiens

<400> SEQUENCE: 7
ttctctcaca cgtgtccggc ctgggctggc tggcctccta cctgccctcc ttcctccgtg     60
tgcccaagtg gattattgcc ctctacacta gcaagttcta accctcctgg tctgacacta    120
cgtctctgct tgtcttctca tttggacttg gtggttcgtc ctgtctcagt gaaacagcag    180
cctttcttgt ttacccatac ccttgatatg aagagaagcc ctctgctgtg tgtccgtggt    240
gagttctggg gtgcgcctag gtcccttctt tgtgccttgg ttttccttgt ccttcttttt    300 acttttttgcc ttagtattga aaaatgctc                                     329
```

<210> SEQ ID NO 8
<211> LENGTH: 491
<212> TYPE: DNA
<213> ORGANISM: Homo sapiens
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (62)..(67)
<223> OTHER INFORMATION: n is a, c, g, or t
<220> FEATURE:
<221> NAME/KEY: misc_feature
<222> LOCATION: (69)..(95)
<223> OTHER INFORMATION: n is a, c, g, or t
<220> FEATURE:
<221> NAME/KEY: misc_feature
<222> LOCATION: (97)..(126)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (302)..(302)
<223> OTHER INFORMATION: n is a, c, g, or t

<400> SEQUENCE: 8

```
tctctctctt tgtgggttgg ccaggaggtt cccccgacca ggttggggag anttngggcn     60
annnnnntnn nnnnnnnnnn nnnnnnnnnn nnnnntnnnn nnnnnnnnnn nnnnnnnnnn    120
nnnnnngatt cccacagcac aaccggtccc ttccatgccc tgggatgcct caccacaccc    180
aggtctcttc ctttgctctg aggtcccttc aaggcctccc caatccaggc caaagcccca    240
tgtgccttgt ccaggaactg cctgggccat gcgaggggcc agcagagggc gccaccnacc    300
anctgacggc tggggaccca cccagcccct ctcccctctc tgctccagac tcacttgcca    360
ttgccaggag atggccccaa caagcacccc gcttttgcag cagaggagct gagttggcag    420
accgggcccc cctgaaccgc acccccatccc accagccccg gccttgcttt gtctggcctc    480
acgtgtctca g                                                        491
```

<210> SEQ ID NO 9
<211> LENGTH: 151
<212> TYPE: DNA
<213> ORGANISM: Homo sapiens
<220> FEATURE:
<221> NAME/KEY: misc_feature
<222> LOCATION: (75)..(93)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t

<400> SEQUENCE: 9

```
tgtcctgggc cctgtgaact gggctgctct ccgtggcagc ggctggtggt gctaaaggct     60
gattttctct cagcnnnnnn nnnnnnnnnn nnnagtttcc tcagagaacc tttcagattn    120
```

```
acaattctgt acttacgttt aatgtctctg a                                    151

<210> SEQ ID NO 10
<211> LENGTH: 205
<212> TYPE: DNA
<213> ORGANISM: Homo sapiens
<220> FEATURE:
<221> NAME/KEY: misc_feature
<222> LOCATION: (156)..(170)
<223> OTHER INFORMATION: n is a, c, g, or t

<400> SEQUENCE: 10
gaacagctcc gggcccggtc tgcctggctg cctccatcac agccctcctg ccctgccagg     60
gagaaagccc aggagctgtc ggactggatc caccagctgg agtctgagaa gttcgacctg   120
atggcgaagc tgaaacagca gaaatatgag atcaannnnn nnnnnnnnnn catcagccac   180
gcccagaagt tccggaaggg ggcag                                          205

<210> SEQ ID NO 11
<211> LENGTH: 398
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (319)..(348)
<223> OTHER INFORMATION: n is a, c, g, or t

<400> SEQUENCE: 11
cactggctga caacctgctg agggtcttcn aggctgtgga acaggccagc aacctcacac     60
aggctcccga ggaggagccc atcccgctgg accagctggg tggctcctgc aggacccatt   120
acggctactc ctctngggct tccagcctcc atcgccactg ggggctcctg ctggcctccc   180
tcgctcccct ggtcctctgt ctgtctctcc tgtgaaacct gggagaccag agtcccnttt   240
agggttcccg gagctccggg aagacccgcc catcccagga ctccagatgc aggagccct   300 gctgcccaca tgcaaggann nnnnnnnnnn nnnnnnnnnn nnnnnnnnac ctgggggggca   360 ggatgcctgg ggacagttca ggacacacac acagtagg                            398

<210> SEQ ID NO 12
<211> LENGTH: 273
<212> TYPE: DNA
<213> ORGANISM: Homo sapiens

<400> SEQUENCE: 12
cattcaagcc ttggaaggga ttaaaaacca actttcgact tctgaaaaga aggctacggg     60
agagtctcca gtgaggggtc tccctgggcc tcatggtctg tctcctctag cctcctgctc   120
atgctgcacg ggcctcccct ccaccctgga cccgctctgt ttctgcctgg tcatcctgag   180
cccctcctgg cctcagggcc attccacagt gctcccctgc ctcaccgctt cctcctcgct   240
cttccagact cttcctgcag aggctccttt ctg                                 273

<210> SEQ ID NO 13
<211> LENGTH: 491
<212> TYPE: DNA
<213> ORGANISM: Homo sapiens
```

```
<220> FEATURE:
<221> NAME/KEY: misc_feature
<222> LOCATION: (56)..(83)
<223> OTHER INFORMATION: n is a, c, g, or t
<220> FEATURE:
<221> NAME/KEY: misc_feature
<222> LOCATION: (231)..(270)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (325)..(354)
<223> OTHER INFORMATION: n is a, c, g, or t

<400> SEQUENCE: 13
cgaagtgcag tttggctcct ggttcgacca cattaagggc tggcttcgga tgaagnnnnn     60
nnnnnnnnnn nnnnnnnnnn nnnacgagga gctgcagcag gacttacagg gctccgtgga    120
gcgcatctgt gggttcctgg gccgtccgct gggcaaggag gcactgggct ccgtcgtggc    180
acactcaacc ttcagcgcca tgaaggccaa caccatgtcc aactcacgc nnnnnnnnnn    240 nnnnnnnnnn nnnnnnnnnn nnnnnnnnnn gccttcctcc ggaaaggggt ctgnggcgac    300
tggaagaacc acttcacggt ggccnnnnnn nnnnnnnnnn nnnnnnnnnn nnnnaagcag    360
atgcggggga tgccgacctt cccctgggat gaagacccgg aggaggacgg cagcccagat    420
cctgagccca gccctgagcc tgagcccaag cccagccttg agcccaacac cagcctggag    480
cgtgagccca g                                                         491

<210> SEQ ID NO 14
<211> LENGTH: 469
<212> TYPE: DNA
<213> ORGANISM: Homo sapiens
<220> FEATURE:
<221> NAME/KEY: misc_feature
<222> LOCATION: (173)..(216)
<223> OTHER INFORMATION: n is a, c, g, or t
<220> FEATURE:
<221> NAME/KEY: misc_feature
<222> LOCATION: (222)..(239)
<223> OTHER INFORMATION: n is a, c, g, or t
<220> FEATURE:
<221> NAME/KEY: misc_feature
<222> LOCATION: (316)..(317)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (324)..(328)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (332)..(341)
<223> OTHER INFORMATION: n is a, c, g, or t
<220> FEATURE:
<221> NAME/KEY: misc_feature
<222> LOCATION: (423)..(424)
<223> OTHER INFORMATION: n is a, c, g, or t
<220> FEATURE:
<221> NAME/KEY: misc_feature
<222> LOCATION: (426)..(427)
<223> OTHER INFORMATION: n is a, c, g, or t
```

```
<400> SEQUENCE: 14
tctgcggtaa aggacttggt ctgttctacc ccctgctcca gcttgccctg ctcgtcctga      60
tcctgtgatt tctctgtcct tggctattct tgcagggagc tggaaaactt cctgaggatt     120
tctggcctcc ccctgggttt tagtttcagg gcacacagga cagcagaaga tcnnnnnnnn     180
nnnnnnnnnn nnnnnnnnnn nnnnnnnnnn nnnnnnagga gnnnnnnnnn nnnnnnnnnt     240
caaagggcct gcagagggag atgtggccct tcctcccct cattgaggac ttaataaatt      300
ggattgatga caccannaan aaannnnnan annnnnnnnn ntggctagga gaggggagga     360
gactggacaa agaagctgga aataggaac tggagttttt aagaaaaatt gttaaagaaa      420
aannanncgc tggttttttg caaatgctgt ataaatctgt catgccaca               469

<210> SEQ ID NO 15
<211> LENGTH: 526
<212> TYPE: DNA
<213> ORGANISM: Homo sapiens
<220> FEATURE:
<221> NAME/KEY: misc_feature
<222> LOCATION: (26)..(52)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (300)..(301)
<223> OTHER INFORMATION: n is a, c, g, or t
<220> FEATURE:
<221> NAME/KEY: misc_feature
<222> LOCATION: (331)..(340)
<223> OTHER INFORMATION: n is a, c, g, or t
<220> FEATURE:
<221> NAME/KEY: misc_feature
<222> LOCATION: (349)..(453)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t

<400> SEQUENCE: 15
aacagcttag tgaggaggca agagcnnnnn nnnnnnnnnn nnnnnnnnnn nnganggcct      60
gtgggcttgc ttttggaang cctcangcag acacgtgccc tctngggtga tgtctgtctg     120
ctgccaggat ggagcagagg agcgccacac atggaggaaa gccctgtaa cgttacctac      180 cttaaactcc actcatcaaa tctgagaaaa gtatccactg gtccccaggg tttcagtcat     240
gcttttgggg gtcattgggt attagagaag taagtatctt ttctgagaga ggggagtcn     300 nccccccta ctgggattc ctctgggctt nnnnnnnnnn attcactcnn nnnnnnnnn       360 nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnccnagcc acacttggag gaaagttgca     480
ggtgggttgg gcaggagca ggcatggttc tgctttgctg tttgtc                    526
```

<210> SEQ ID NO 16
<211> LENGTH: 323
<212> TYPE: DNA
<213> ORGANISM: Homo sapiens
<220> FEATURE:
<221> NAME/KEY: misc_feature
<222> LOCATION: (72)..(172)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (278)..(278)
<223> OTHER INFORMATION: n is a, c, g, or t

<400> SEQUENCE: 16
gatcgctgag ctagagatga ccatcttcct catcaatatg ctggagaact tcagagttga      60
aatccaacac cnnnnnnnnn nnnnnnnnnn nnnnnnnnnn nnnnnnnnnn nnnnnnnnn     120 nnnnnnnnnn nnnnnnnnnn nnnnnnnnnn nnnnnnnnnn nnnnnnnnnn nnaganagga     180
tngcctgcag ccacatggga ggaaggccca ggggtggggc ccatgggtc tctgcatctt      240 cagtcgtctg tcccaagtcc tgctcctttc tgcccagnct gctcagcagg ttgaatgggt     300
tctcagtggt caccttcctc agc                                            323

<210> SEQ ID NO 17
<211> LENGTH: 495
<212> TYPE: DNA
<213> ORGANISM: Homo sapiens

<400> SEQUENCE: 17
cctcaggtgt agctgagctg tgacattgct ggtcatcctt ggtgctcttg cttttttgaa      60
agatgctttt ttttttttta actgacgtag aatgaagaac tgcatgtggc ttctctgtct     120
ctgtggaaaa gccatctcag gttggcggca gacacattgt catcagaggg gagcagcggc     180
tctggtcctc ggagctggtt cctctctccc accctaaggg cagccctcca tggtcctgtc     240
tgtccttctg aagtgtgtcc atcctgacct gcgggtcctc agctgctccc acacttgtgc     300
cagcccggag gggactggtc ccggtcaccg cggacgtgct ggccttggta tgtgccaggc     360
ttgcctgggc tgggcagcct tggggggggct gcctttgtgg tgggcgctgg ggaagtacgt     420
cccagcggcc tcagggtcta aggagcgcta gtgccttgcc cacaggtgcg ggaccatctg     480
atgtgatgtg aatac                                                    495

<210> SEQ ID NO 18
<211> LENGTH: 337
<212> TYPE: DNA
<213> ORGANISM: Homo sapiens
<220> FEATURE:
<221> NAME/KEY: misc_feature
<222> LOCATION: (60)..(134)
<223> OTHER INFORMATION: n is a, c, g, or t

<400> SEQUENCE: 18
gaccgtgcag tctgcgcttt cctctcccgc ctgcctagcc caggatgaag ggctgggtgn      60
nnnnnnnnnn nnnnnnnnnn nnnnnnnnnn nnnnnnnnnn nnnnnnnnnn nnnnnnnnn     120

```
nnnnnnnnnn nnnntggtcc cctcttttgg ggtagatgcg gccccgatca ggcctgactc      180
gctgctcttt ttgttcccct ctgtctgctc gaaccacttg cctcgggcta atccctccct      240
cttcctccac ccggcactgg ggaagtcaag aatggggcct ggggctctca gggagaactg      300
cttcccctgg cagagctggg tggcagctct tcctccc                                337

<210> SEQ ID NO 19
<211> LENGTH: 553
<212> TYPE: DNA
<213> ORGANISM: Homo sapiens

<400> SEQUENCE: 19
cccctgggga ctctgtcaga ggctccatgg aggcctctca agtccaagtg cctctggaag       60
cctctccaat tacattccca ccaccctgtg ccccagaaag gccccccatc agcccagtcc      120
caggcgcccg tcaagcaggc ctctgagagt gctacccttc tcttgtaacc ttgcagccaa      180
cacccctgcc cggcccctga gctgcctcct ccagcccatg ctcttacagg ccctgcacag      240
agtagcactc attaattctt ggttaaggaa tgaatcaacg aatgaatggc tatgcatgga      300
cctctgggca gggagacctg ggtcttctct ggctgagagg ggaaggctaa ggcatggctg      360
agattcaagc caccattcca ggcctctttg cccaagaaag aaacttctgt caccсcttgca     420 ctctcctgtg ttctgagtcc ctggccaata gcacagcctt ccatgccccg acccccaccc     480
caagcctctc cactaggcct ctgccaggat ctaagcccat gagcacaggg actggctatc      540
ccaagacctg gca                                                        553

<210> SEQ ID NO 20
<211> LENGTH: 482
<212> TYPE: DNA
<213> ORGANISM: Homo sapiens
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (114)..(129)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (349)..(349)
<223> OTHER INFORMATION: n is a, c, g, or t

<400> SEQUENCE: 20
gaaactgcgc attctctagt agtatatatc gtgcctgtct tcaaaaacat ttnccttttt       60
atactcattc cccccaggca tggggtagtg tcagtcggac tgcacagggn aacnnnnnnn      120
nnnnnnnnnt ttggncccct actcgggaaa cgtctgcctg ttctcgatgg tgatggggtg      180
gctgccattc ccttggtttt cctaagcccct ttctaacgag agtctcaaac aagcggaggc      240
gagggccaat tcaaccccat tctttccagc gccccgcacc atagcacctg ccacctgag       300 aaccaggaac gcaccctctc tgtggagctc tgactggtgt agctggaanc aaacagcaac      360
```

```
ttgcaaacgg acgaagagcc tgccgtgtgt taatcatttg ccttacaaga tgtaccagac    420
ggtttccagt actaacaaag ggaataaaaa tacctcacgc cacaatccag catattgatg    480
tt                                                                   482
```